US008168392B2

(12) United States Patent
Sugiura

(10) Patent No.: US 8,168,392 B2
(45) Date of Patent: May 1, 2012

(54) TETRAHYDROFOLATE SYNTHETASE GENE

(75) Inventor: Takeyuki Sugiura, Edogawa-ku (JP)

(73) Assignee: Daiichi Sankyo Co., Ltd., Tokyo (JP)

( * ) Notice: Subject to any disclaimer, the term of this patent is extended or adjusted under 35 U.S.C. 154(b) by 430 days.

(21) Appl. No.: 12/420,702

(22) Filed: Apr. 8, 2009

(65) Prior Publication Data

US 2009/0226936 A1 Sep. 10, 2009

Related U.S. Application Data

(62) Division of application No. 10/573,969, filed as application No. PCT/JP2004/014812 on Sep. 30, 2004, now Pat. No. 7,534,562.

(30) Foreign Application Priority Data

Sep. 30, 2003 (JP) ................................ 2003-341245

(51) Int. Cl.
| | |
|---|---|
| C12Q 1/68 | (2006.01) |
| G01N 33/53 | (2006.01) |
| C12N 9/06 | (2006.01) |
| C12N 15/00 | (2006.01) |
| C12P 21/06 | (2006.01) |
| C07H 21/04 | (2006.01) |

(52) U.S. Cl. ....... 435/6.14; 435/7.2; 435/69.1; 435/191; 435/325; 536/23.2

(58) Field of Classification Search .................. None
See application file for complete search history.

(56) References Cited

FOREIGN PATENT DOCUMENTS
| | | | |
|---|---|---|---|
| JP | 2005-006658 A | 1/2005 |
| JP | 2006-517094 A | 7/2006 |
| JP | 2006-517788 A | 8/2006 |
| WO | 02/083873 A2 | 10/2002 |
| WO | 2004/080148 A2 | 9/2004 |

OTHER PUBLICATIONS

Sugiura et al. A novel mitochondrial C1-tetrahydrofolate synthetase is upregulated in human colon adenocarcinoma, Biochem Biophys Res Commun. Feb. 27, 2004;315(1):204-11, available online Jan. 24, 2004.*
Li et al. Inability of leucovorin to rescue a naturally methotrexate-resistant human soft tissue sarcoma cell line from trimetrexate cytotoxicity, Cancer Res. Dec. 15, 1992;52(24):6866-70.*
Takeyuki Sugiura et al., "A novel mitochondrial $C_1$-tetrahydrofolate synthetase is upregulated in human colon adenocarcinoma", Biochemical and Biophysical Research Communications, 2004, 315: 204-211.
Carl Branden et al., "Introduction to Protein Structure", Gerald Publishing Inc., New York, 1991, p. 247.
Andrzej Witkowski et al., "Conversion of a β-Ketoacyl Synthase to a Malonyl Decarboxylase by Replacement of the Active-Site Cysteine with Glutamine", Biochemistry, 1999, 38: 11643-11650.
Jennifer L. Seffernick et al., "Melamine Deaminase and Atrazine Chlorohydrolase: 98 Percent Identical but Functionally Different", Journal of Bacteriology, 2001, 183(8): 2405-2410.
Dean W. Hum et al., "Primary Structure of a Human Trifunctional Enzyme", The Journal of Biological Chemistry, 1988, 263(31): 15946-1950.
Chuck Staben et al., "Nucleotide Sequence of the *Saccharomyces cerevisiae* ADE3 Gene Encoding $C_1$-Tetrahydrofolate Synthase", The Journal of Biological Chemistry, 1986, 261(10): 4629-4637.
Karen W. Shannon et al., "Purification and Characterization of a Mitochondrial Isozyme of $C_1$-Tetrahydrofolate Synthase from *Saccharomyces cerevisiae*", The Journal of Biological Chemistry, 1986, 261(26): 12266-12271.
Anice E. Thigpen et al., "Rat $C_1$-Tetrahydrofolate Synthase", The Journal of Biological Chemistry, 1990, 265(14): 7907-7913.
Inderjit K. Dev et al., "A Complex of $N^5,N^{10}$-Methylenetetrahydrofolate Dehydrogenase and $N^5,N^{10}$-Methenyltetrahydrofolate Cyclohydrolase in *Escherichia coli*", 1978, 253(12): 4245-4253.
S.K. Raj et al., "Reverse Transcription-Polymerase Chain Reaction (RT-PCR) for Direct Detection of Cucumber Mosaic Virus (CMV) in Gladiolus", Biochemistry and Molecular Biology International, 1998, 44(1): 89-95.
Michael A. Frohman et al., "Rapid production of full-length cDNAs from rare transcripts: Amplification using a single gene-specific oligonucleotide primer", Proc. Natl. Acad. Sci, 1988, 85: 8998-9002.
F. Sanger et al., "DNA sequencing with chain-terminating inhibitors", Proc. Natl. Acad. Sci., 1977, 74(12): 5463-5467.
Allan M. Maxam et al., "Sequencing End-Labeled DNA with Base-Specific Chemical Cleavages", Methods in Enzymology, 1980, 65: 499-560.
Manuel G. Claros et al., "Computational method to predict mitochondrially imported proteins and their targeting sequences", Eur. J. Biochem., 1996, 241: 779-786.
Paul J. Kim et al., "Survivin and molecular pathogenesis of colorectal cancer", The Lancet, 2003, 362: 205-209.
Rachel H. Giles et al., "Caught up in a Wnt Storm: Wnt signaling in cancer", Biochimica et Biophysica Acta, 2003, 1653: 1-24.
Tong-Chuan He et al., "Identification of c-*MYC* as a Target of the APC Pathway", Science, 1998, 281: 1509-1512.
David L. Levens, "Reconstructing MYC", Genes & Development, 2003, 17: 1071-1077.

(Continued)

*Primary Examiner* — Anand Desai
*Assistant Examiner* — Iqbal H Chowdhury
(74) *Attorney, Agent, or Firm* — Sughrue Mion, PLLC

(57) ABSTRACT

By finding a novel tetrahydrofolate synthetase gene and a protein encoded by said gene, a method for identifying a compound which inhibits cell growth accelerating activity of said protein is provided, and a judging method, a preventing method and a treating method of colon cancer are provided. A DNA comprising a nucleotide sequence of from the 94th to 2934th positions of the nucleotide sequence of SEQ ID NO:1 of the SEQUENCE LISTING; a polynucleotide which specifically hybridizes with said DNA; a protein encoded by said DNA; a recombinant vector comprising said DNA; a transformant comprising said recombinant vector; an antibody for said protein; a method for producing said protein; a method for identifying a compound which inhibits cell growth accelerating activity possessed by said protein; a method for judging colon cancer, characterizing in that expressed amount of said DNA is measured; a kit for judging colon cancer; a preventive agent and/or therapeutic agent for colon cancer.

2 Claims, 7 Drawing Sheets

OTHER PUBLICATIONS

Timothy A. Garrow et al., "Cloning of Human cDNAs Encoding Mitochondrial and Cytosolic Serine Hydroxymethyltransferases and Chromosomal Localization", The Journal of Biological Chemistry, 1993, 268(16): 11910-11916.

Mikhail A. Nikiforov et al., "A Functional Screen for Myc-Responsive Genes Reveals Serine Hydroxymethyltransferase, a Major Source of the One-Carbon Unit for Cell Metabolism", Molecular and Cellular Biology, 2002, 22(16): 5793-5800.

Sean V. Tavtigian et al., "Cloning of Mid-$G_1$ Serum Response Genes and Identification of a Subset Regulated by Conditional myc Expression", Molecular Biology of the Cell, 1994, 5: 375-388.

Enrique Villar et al., "$C_1$-Tetrahydrofolate Synthase from Rabbit Liver", The Journal of Biological Chemistry, 1985, 260(4): 2245-2252.

Priya Prasannan et al., "Human Mitochondrial $C_1$-Tetrahydrofolate Synthase", The Journal of Biological Chemistry, 2003, 278(44): 43178-43187.

International Search Report issued in PCT/JP2004/014812 on Nov. 16, 2004.

Japanese Office Action dated Apr. 27, 2010, in corresponding Japanese Application No. 2005-514328.

Japanese Office Action dated Aug. 3, 2010 issued in application No. 2005-514328.

* cited by examiner

ND: N-TERMINAL MOIETY DNA
NT: N-TERMINAL DEFICIENT DNA
SP: TARGET SEQUENCE (SIGNAL PEPTIDE)

1: COLON CANCER CELL HCT116
2: COLON CANCER CELL SE620
3: NORMAL COLON CELL CCD841CoN

DKFZP: EXPRESSION QUANTITY OF THE GENE TO BE
 PROVIDED BY THE INVENTION
GAPDH: EXPRESSION QUANTITY OF GLYCERALDEHYDE
 3-PHOSPHATE DEHYDROGENASE

-: AN ANIMAL CELL DERIVED SAMPLE OF NO GENE TRANSFER

E: AN ANIMAL CELL DERIVED SAMPLE IN WHICH pCMV-TAG4 VECTOR WAS TRANSFERRED

FL: AN ANIMAL CELL DERIVED SAMPLE IN WHICH THE RECOMBINANT pCMV-TAG4 VECTOR CONCERNED IN THE DNA TO BE PROVIDED BY THE INVENTION WAS TRANSFERRED

DKFZP: GROWTH OF AN ANIMAL CELL INTO WHICH THE RECOMBINANT pCMV-TAG4 VECTOR CONCERNED IN THE DNA TO BE PROVIDED BY THE INVENTION WAS TRANSFERRED

EMPTY VECTOR: GROWTH OF THE ANIMAL CELL INTO WHICH pCMV-TAG4 VECTOR WAS TRANSFERRED

β CATENIN ACTIVATION c-myc TRANSCRIPTION mt C1-THFS INDUCTION
(mt SHMT INDUCTION)

MITOCHONDRIAL C1 METABOLISM ACTIVATION

SEQUENCE LISTING

<160> NUMBER OF SEQ ID NOS: 7

<210> SEQ ID NO 1
<211> LENGTH: 2934
<212> TYPE: DNA
<213> ORGANISM: Homo sapiens
<220> FEATURE:
<221> NAME/KEY: CDS
<222> LOCATION: (1)..(2934)
<220> FEATURE:
<221> NAME/KEY: sig_peptide
<222> LOCATION: (1)..(93)

<400> SEQUENCE: 1

```
atg ggc acg cgt ctg ccg ctc gtc ctg cgc cag ctc cgc cgc ccc        48
Met Gly Thr Arg Leu Pro Leu Val Leu Arg Gln Leu Arg Arg Pro
1               5                   10                  15 cag ccc ccg ggc cct ccg cgc cgc ctc cgt gtg ccc tgt cgc gct agc    96
Gln Pro Pro Gly Pro Pro Arg Arg Leu Arg Val Pro Cys Arg Ala Ser
                20                  25                  30 agc ggc ggc ggc gga ggc ggc ggc ggt ggc cgg gag ggc ctg ctt gga   144
Ser Gly Gly Gly Gly Gly Gly Gly Gly Arg Glu Gly Leu Leu Gly
            35                  40                  45 cag cgg cgg ccg cag gat ggc cag gcc cgg agc agc tgc agc ccc ggc   192
Gln Arg Arg Pro Gln Asp Gly Gln Ala Arg Ser Ser Cys Ser Pro Gly
        50                  55                  60 ggc cga acg ccc gcg gcg cgg gac tcc atc gtc aga gaa gtc att cag   240
Gly Arg Thr Pro Ala Ala Arg Asp Ser Ile Val Arg Glu Val Ile Gln
65                  70                  75                  80 aat tca aaa gaa gtt cta agt tta ttg caa gaa aaa aac cct gcc ttc   288
Asn Ser Lys Glu Val Leu Ser Leu Leu Gln Glu Lys Asn Pro Ala Phe
                85                  90                  95 aag ccg gtt ctt gca att atc cag gca ggt gac gac aac ttg atg cag   336
Lys Pro Val Leu Ala Ile Ile Gln Ala Gly Asp Asp Asn Leu Met Gln
                100                 105                 110 gaa atc aac cag aat ttg gct gag gag gct ggt ctg aac atc act cac   384
Glu Ile Asn Gln Asn Leu Ala Glu Glu Ala Gly Leu Asn Ile Thr His
            115                 120                 125 att tgc ctc cct cca gat agc agt gaa gcc gag att ata gat gaa atc   432
Ile Cys Leu Pro Pro Asp Ser Ser Glu Ala Glu Ile Ile Asp Glu Ile
        130                 135                 140 tta aag atc aat gaa gat acc aga gta cat ggc ctt gcc ctt cag atc   480
Leu Lys Ile Asn Glu Asp Thr Arg Val His Gly Leu Ala Leu Gln Ile
145                 150                 155                 160 tct gag aac ttg ttt agc aac aaa gtc ctc aat gcc ttg aaa cca gaa   528
Ser Glu Asn Leu Phe Ser Asn Lys Val Leu Asn Ala Leu Lys Pro Glu
                165                 170                 175 aaa gat gtg gat gga gta aca gac ata aac ctg ggg aag ctg gtg cga   576
Lys Asp Val Asp Gly Val Thr Asp Ile Asn Leu Gly Lys Leu Val Arg
                180                 185                 190 ggg gat gcc cat gaa tgt ttt gtt tca cct gtt gcc aaa gct gta att   624
Gly Asp Ala His Glu Cys Phe Val Ser Pro Val Ala Lys Ala Val Ile
            195                 200                 205 gaa ctt ctt gaa aaa tca ggt gtc aac cta gat gga aag aag att ttg   672
Glu Leu Leu Glu Lys Ser Gly Val Asn Leu Asp Gly Lys Lys Ile Leu
        210                 215                 220 gta gtg ggg gcc cat ggg tct ttg gaa gct gct cta caa tgc ctg ttc   720
Val Val Gly Ala His Gly Ser Leu Glu Ala Ala Leu Gln Cys Leu Phe
225                 230                 235                 240 cag aga aaa ggg tcc atg aca atg agc atc cag tgg aaa aca cgc cag   768
Gln Arg Lys Gly Ser Met Thr Met Ser Ile Gln Trp Lys Thr Arg Gln
```

|     |     |
| --- | --- |
| ctt caa agc aag ctt cac gag gct gac att gtg gtc cta ggc tca cct<br>Leu Gln Ser Lys Leu His Glu Ala Asp Ile Val Val Leu Gly Ser Pro<br>260 265 270 | 816 |
| aag cca gaa gag att ccc ctt act tgg ata caa cca gga act act gtt<br>Lys Pro Glu Glu Ile Pro Leu Thr Trp Ile Gln Pro Gly Thr Thr Val<br>275 280 285 | 864 |
| ctc aac tgc tcc cat gac ttc ctg tca ggg aag gtt ggg tgt ggc tct<br>Leu Asn Cys Ser His Asp Phe Leu Ser Gly Lys Val Gly Cys Gly Ser<br>290 295 300 | 912 |
| cca aga ata cat ttt ggt gga ctc att gag gaa gat gat gtg att ctc<br>Pro Arg Ile His Phe Gly Gly Leu Ile Glu Glu Asp Asp Val Ile Leu<br>305 310 315 320 | 960 |
| ctt gct gca gct ctg cga att cag aac atg gtc agt agt gga agg aga<br>Leu Ala Ala Ala Leu Arg Ile Gln Asn Met Val Ser Ser Gly Arg Arg<br>325 330 335 | 1008 |
| tgg ctt cgt gaa cag cag cac agg cgg tgg aga ctt cac tgc ttg aaa<br>Trp Leu Arg Glu Gln Gln His Arg Arg Trp Arg Leu His Cys Leu Lys<br>340 345 350 | 1056 |
| ctt cag cct ctc tcc cct gtg cca agt gac att gag att tca aga gga<br>Leu Gln Pro Leu Ser Pro Val Pro Ser Asp Ile Glu Ile Ser Arg Gly<br>355 360 365 | 1104 |
| caa act cca aaa gct gtg gat gtc ctt gcc aag gag att gga ttg ctt<br>Gln Thr Pro Lys Ala Val Asp Val Leu Ala Lys Glu Ile Gly Leu Leu<br>370 375 380 | 1152 |
| gca gat gaa att gaa atc tat ggc aaa agc aaa gcc aaa gta cgt ttg<br>Ala Asp Glu Ile Glu Ile Tyr Gly Lys Ser Lys Ala Lys Val Arg Leu<br>385 390 395 400 | 1200 |
| tcc gtg cta gaa agg tta aag gat caa gca gat gga aaa tac gtc tta<br>Ser Val Leu Glu Arg Leu Lys Asp Gln Ala Asp Gly Lys Tyr Val Leu<br>405 410 415 | 1248 |
| gtt gct ggg atc aca ccc acc cct ctt gga gaa ggg aag agc aca gtc<br>Val Ala Gly Ile Thr Pro Thr Pro Leu Gly Glu Gly Lys Ser Thr Val<br>420 425 430 | 1296 |
| acc atc ggg ctt gtg cag gct ctg acc gca cac ctg aat gtc aac tcc<br>Thr Ile Gly Leu Val Gln Ala Leu Thr Ala His Leu Asn Val Asn Ser<br>435 440 445 | 1344 |
| ttt gcc tgc ttg agg cag cct tcc caa gga ccg acg ttt gga gtg aaa<br>Phe Ala Cys Leu Arg Gln Pro Ser Gln Gly Pro Thr Phe Gly Val Lys<br>450 455 460 | 1392 |
| gga gga gcc gcg ggt ggt gga tat gcc cag gtc atc ccc atg gag gag<br>Gly Gly Ala Ala Gly Gly Gly Tyr Ala Gln Val Ile Pro Met Glu Glu<br>465 470 475 480 | 1440 |
| ttc aac ctt cac ttg act gga gac atc cac gcc atc acc gct gcc aat<br>Phe Asn Leu His Leu Thr Gly Asp Ile His Ala Ile Thr Ala Ala Asn<br>485 490 495 | 1488 |
| aac ttg ctg gct gcc gcc atc gac acg agg att ctt cat gaa aac acg<br>Asn Leu Leu Ala Ala Ala Ile Asp Thr Arg Ile Leu His Glu Asn Thr<br>500 505 510 | 1536 |
| caa aca gat aag gct ctg tat aat cgg ctg gtt cct tta gtg aat ggt<br>Gln Thr Asp Lys Ala Leu Tyr Asn Arg Leu Val Pro Leu Val Asn Gly<br>515 520 525 | 1584 |
| gtc aga gaa ttt tca gaa att cag ctt gct cgg cta aaa aaa ctg gga<br>Val Arg Glu Phe Ser Glu Ile Gln Leu Ala Arg Leu Lys Lys Leu Gly<br>530 535 540 | 1632 |
| ata aat aag act gat ccg agc aca ctg aca gaa gag gaa gtg agt aaa<br>Ile Asn Lys Thr Asp Pro Ser Thr Leu Thr Glu Glu Glu Val Ser Lys<br>545 550 555 560 | 1680 |
| ttt gcc cgt ctc gac atc gac cca tct acc atc acg tgg cag aga gta<br>Phe Ala Arg Leu Asp Ile Asp Pro Ser Thr Ile Thr Trp Gln Arg Val | 1728 |

|  |  |
|---|---|
| ttg gat aca aat gac cga ttt cta cga aaa ata acc atc ggg cag gga<br>Leu Asp Thr Asn Asp Arg Phe Leu Arg Lys Ile Thr Ile Gly Gln Gly<br>565                      570                    575 | 1776 |
| aac aca gag aag ggc cat tac cgg cag gcg cag ttt gac atc gca gtg<br>Asn Thr Glu Lys Gly His Tyr Arg Gln Ala Gln Phe Asp Ile Ala Val<br>580                      585                    590 | 1824 |
| gcc agc gag atc atg gcg gtg ctg gcc ctg acg gac agc ctc gca gac<br>Ala Ser Glu Ile Met Ala Val Leu Ala Leu Thr Asp Ser Leu Ala Asp<br>595                      600                    605 | 1872 |
| atg aag gca cgg ctg gga agg atg gtg gtg gcc agt gac aaa agc ggg<br>Met Lys Ala Arg Leu Gly Arg Met Val Val Ala Ser Asp Lys Ser Gly<br>610                      615                    620 | 1920 |
| cag cct gtg aca gca gat gat ttg ggg gtg aca ggt gct ttg aca gtt<br>Gln Pro Val Thr Ala Asp Asp Leu Gly Val Thr Gly Ala Leu Thr Val<br>625                      630                    635                    640 | 1968 |
| ttg atg aaa gat gca ata aaa cca aac ctg atg cag acc ctg gaa ggg<br>Leu Met Lys Asp Ala Ile Lys Pro Asn Leu Met Gln Thr Leu Glu Gly<br>645                      650                    655 | 2016 |
| aca cct gtg ttc gtg cat gcg ggc cct ttt gct aac att gct cac ggc<br>Thr Pro Val Phe Val His Ala Gly Pro Phe Ala Asn Ile Ala His Gly<br>660                      665                    670 | 2064 |
| aac tct tca gtg ttg gct gat aaa att gcc ctg aaa ctg gtt ggt gaa<br>Asn Ser Ser Val Leu Ala Asp Lys Ile Ala Leu Lys Leu Val Gly Glu<br>675                      680                    685 | 2112 |
| gaa gga ttt gta gtg acc gaa gct ggc ttt ggt gct gac atc gga atg<br>Glu Gly Phe Val Val Thr Glu Ala Gly Phe Gly Ala Asp Ile Gly Met<br>690                      695                    700 | 2160 |
| gag aaa ttc ttc aac atc aag tgc cga gct tcc ggc ttg gtg ccc aac<br>Glu Lys Phe Phe Asn Ile Lys Cys Arg Ala Ser Gly Leu Val Pro Asn<br>705                      710                    715                    720 | 2208 |
| gtg gtt gtg tta gtg gca acg gtg cga gct ctg aag atg cat gga ggc<br>Val Val Val Leu Val Ala Thr Val Arg Ala Leu Lys Met His Gly Gly<br>725                      730                    735 | 2256 |
| ggg cca agt gta acg gct ggt gtt cct ctt aag aaa gaa tat aca gag<br>Gly Pro Ser Val Thr Ala Gly Val Pro Leu Lys Lys Glu Tyr Thr Glu<br>740                      745                    750 | 2304 |
| gag aac atc cag ctg gtg gca gac ggc tgc tgt aac ctc cag aag caa<br>Glu Asn Ile Gln Leu Val Ala Asp Gly Cys Cys Asn Leu Gln Lys Gln<br>755                      760                    765 | 2352 |
| att cag atc act cag ctc ttt ggg gtt ccc gtt gtg gtg gct ctg aat<br>Ile Gln Ile Thr Gln Leu Phe Gly Val Pro Val Val Val Ala Leu Asn<br>770                      775                    780 | 2400 |
| gtc ttc aag acc gac acc cgc gct gag att gac ttg gtg tgt gag ctt<br>Val Phe Lys Thr Asp Thr Arg Ala Glu Ile Asp Leu Val Cys Glu Leu<br>785                      790                    795                    800 | 2448 |
| gca aag cgg gct ggt gcc ttt gat gca gtc ccc tgc tat cac tgg tcg<br>Ala Lys Arg Ala Gly Ala Phe Asp Ala Val Pro Cys Tyr His Trp Ser<br>805                      810                    815 | 2496 |
| gtt ggt gga aaa gga tcg gtg gac ttg gct cgg gct gtg aga gag gct<br>Val Gly Gly Lys Gly Ser Val Asp Leu Ala Arg Ala Val Arg Glu Ala<br>820                      825                    830 | 2544 |
| gcg agt aaa aga agc cga ttc cag ttc ctg tat gat gtt cag gtt cca<br>Ala Ser Lys Arg Ser Arg Phe Gln Phe Leu Tyr Asp Val Gln Val Pro<br>835                      840                    845 | 2592 |
| att gtg gac aag ata agg acc att gct cag gct gtc tat gga gcc aaa<br>Ile Val Asp Lys Ile Arg Thr Ile Ala Gln Ala Val Tyr Gly Ala Lys<br>850                      855                    860 | 2640 |
| gat att gaa ctc tct cct gag gca caa gcc aaa ata gat cgt tac act<br>Asp Ile Glu Leu Ser Pro Glu Ala Gln Ala Lys Ile Asp Arg Tyr Thr | 2688 |

|     |     |     |     |     |     |     |     |     |     |     |     |      |
|-----|-----|-----|-----|-----|-----|-----|-----|-----|-----|-----|-----|------|
|     |     | 885 |     |     |     | 890 |     |     |     | 895 |     |      |
| caa | cag | ggt | ttt | gga | aat | ttg | ccc | atc | tgc | atg | gca | aag acc cac ctt | 2736 |
| Gln | Gln | Gly | Phe | Gly | Asn | Leu | Pro | Ile | Cys | Met | Ala | Lys Thr His Leu |      |
|     |     | 900 |     |     |     | 905 |     |     |     | 910 |     |      |
| tct | cta | tct | cac | caa | cct | gac | aaa | aaa | ggt | gtg | cca | agg gac ttc atc | 2784 |
| Ser | Leu | Ser | His | Gln | Pro | Asp | Lys | Lys | Gly | Val | Pro | Arg Asp Phe Ile |      |
|     |     | 915 |     |     |     | 920 |     |     |     | 925 |     |      |
| tta | cct | atc | agt | gac | gtc | cgg | gcc | agc | ata | ggc | gct | ggg ttc att tac | 2832 |
| Leu | Pro | Ile | Ser | Asp | Val | Arg | Ala | Ser | Ile | Gly | Ala | Gly Phe Ile Tyr |      |
|     |     | 930 |     |     |     | 935 |     |     |     | 940 |     |      |
| cct | ttg | gtc | gga | acg | atg | agc | acc | atg | cca | gga | ctg | ccc acc cgg ccc | 2880 |
| Pro | Leu | Val | Gly | Thr | Met | Ser | Thr | Met | Pro | Gly | Leu | Pro Thr Arg Pro |      |
| 945 |     |     |     |     | 950 |     |     |     |     | 955 |     | 960  |
| tgc | ttt | tat | gac | ata | gat | ctt | gat | acc | gaa | aca | gaa | caa gtt aaa ggc | 2928 |
| Cys | Phe | Tyr | Asp | Ile | Asp | Leu | Asp | Thr | Glu | Thr | Glu | Gln Val Lys Gly |      |
|     |     |     |     | 965 |     |     |     | 970 |     |     |     | 975  |
| ttg | ttc |     |     |     |     |     |     |     |     |     |     |      | 2934 |
| Leu | Phe |     |     |     |     |     |     |     |     |     |     |      |      |

<210> SEQ ID NO 2
<211> LENGTH: 978
<212> TYPE: PRT
<213> ORGANISM: Homo sapiens

<400> SEQUENCE: 2

Met Gly Thr Arg Leu Pro Leu Val Leu Arg Gln Leu Arg Arg Pro Pro
1               5                   10                  15

Gln Pro Pro Gly Pro Pro Arg Arg Leu Arg Val Pro Cys Arg Ala Ser
            20                  25                  30

Ser Gly Gly Gly Gly Gly Gly Gly Gly Arg Glu Gly Leu Leu Gly
        35                  40                  45

Gln Arg Arg Pro Gln Asp Gly Gln Ala Arg Ser Ser Cys Ser Pro Gly
    50                  55                  60

Gly Arg Thr Pro Ala Ala Arg Asp Ser Ile Val Arg Glu Val Ile Gln
65                  70                  75                  80

Asn Ser Lys Glu Val Leu Ser Leu Leu Gln Glu Lys Asn Pro Ala Phe
                85                  90                  95

Lys Pro Val Leu Ala Ile Ile Gln Ala Gly Asp Asp Asn Leu Met Gln
            100                 105                 110

Glu Ile Asn Gln Asn Leu Ala Glu Glu Ala Gly Leu Asn Ile Thr His
        115                 120                 125

Ile Cys Leu Pro Pro Asp Ser Ser Glu Ala Glu Ile Ile Asp Glu Ile
    130                 135                 140

Leu Lys Ile Asn Glu Asp Thr Arg Val His Gly Leu Ala Leu Gln Ile
145                 150                 155                 160

Ser Glu Asn Leu Phe Ser Asn Lys Val Leu Asn Ala Leu Lys Pro Glu
                165                 170                 175

Lys Asp Val Asp Gly Val Thr Asp Ile Asn Leu Gly Lys Leu Val Arg
            180                 185                 190

Gly Asp Ala His Glu Cys Phe Val Ser Pro Val Ala Lys Ala Val Ile
        195                 200                 205

Glu Leu Leu Glu Lys Ser Gly Val Asn Leu Asp Gly Lys Lys Ile Leu
    210                 215                 220

Val Val Gly Ala His Gly Ser Leu Glu Ala Ala Leu Gln Cys Leu Phe
225                 230                 235                 240

Gln Arg Lys Gly Ser Met Thr Met Ser Ile Gln Trp Lys Thr Arg Gln
                245                 250                 255

```
Leu Gln Ser Lys Leu His Glu Ala Asp Ile Val Val Leu Gly Ser Pro
            260                 265                 270
Lys Pro Glu Glu Ile Pro Leu Thr Trp Ile Gln Pro Gly Thr Thr Val
            275                 280                 285
Leu Asn Cys Ser His Asp Phe Leu Ser Gly Lys Val Gly Cys Gly Ser
290                 295                 300
Pro Arg Ile His Phe Gly Gly Leu Ile Glu Glu Asp Asp Val Ile Leu
305                 310                 315                 320
Leu Ala Ala Ala Leu Arg Ile Gln Asn Met Val Ser Ser Gly Arg Arg
                325                 330                 335
Trp Leu Arg Glu Gln Gln His Arg Arg Trp Arg Leu His Cys Leu Lys
                340                 345                 350
Leu Gln Pro Leu Ser Pro Val Pro Ser Asp Ile Glu Ile Ser Arg Gly
                355                 360                 365
Gln Thr Pro Lys Ala Val Asp Val Leu Ala Lys Glu Ile Gly Leu Leu
        370                 375                 380
Ala Asp Glu Ile Glu Ile Tyr Gly Lys Ser Lys Ala Lys Val Arg Leu
385                 390                 395                 400
Ser Val Leu Glu Arg Leu Lys Asp Gln Ala Asp Gly Lys Tyr Val Leu
                405                 410                 415
Val Ala Gly Ile Thr Pro Thr Pro Leu Gly Glu Gly Lys Ser Thr Val
                420                 425                 430
Thr Ile Gly Leu Val Gln Ala Leu Thr Ala His Leu Asn Val Asn Ser
            435                 440                 445
Phe Ala Cys Leu Arg Gln Pro Ser Gln Gly Pro Thr Phe Gly Val Lys
450                 455                 460
Gly Gly Ala Ala Gly Gly Gly Tyr Ala Gln Val Ile Pro Met Glu Glu
465                 470                 475                 480
Phe Asn Leu His Leu Thr Gly Asp Ile His Ala Ile Thr Ala Ala Asn
                485                 490                 495
Asn Leu Leu Ala Ala Ala Ile Asp Thr Arg Ile Leu His Glu Asn Thr
            500                 505                 510
Gln Thr Asp Lys Ala Leu Tyr Asn Arg Leu Val Pro Leu Val Asn Gly
            515                 520                 525
Val Arg Glu Phe Ser Glu Ile Gln Leu Ala Arg Leu Lys Lys Leu Gly
        530                 535                 540
Ile Asn Lys Thr Asp Pro Ser Thr Leu Thr Glu Glu Val Ser Lys
545                 550                 555                 560
Phe Ala Arg Leu Asp Ile Asp Pro Ser Thr Ile Thr Trp Gln Arg Val
                565                 570                 575
Leu Asp Thr Asn Asp Arg Phe Leu Arg Lys Ile Thr Ile Gly Gln Gly
            580                 585                 590
Asn Thr Glu Lys Gly His Tyr Arg Gln Ala Gln Phe Asp Ile Ala Val
            595                 600                 605
Ala Ser Glu Ile Met Ala Val Leu Ala Leu Thr Asp Ser Leu Ala Asp
        610                 615                 620
Met Lys Ala Arg Leu Gly Arg Met Val Val Ala Ser Asp Lys Ser Gly
625                 630                 635                 640
Gln Pro Val Thr Ala Asp Asp Leu Gly Val Thr Gly Ala Leu Thr Val
                645                 650                 655
Leu Met Lys Asp Ala Ile Lys Pro Asn Leu Met Gln Thr Leu Glu Gly
                660                 665                 670
Thr Pro Val Phe Val His Ala Gly Pro Phe Ala Asn Ile Ala His Gly
```

675                 680                 685
Asn Ser Ser Val Leu Ala Asp Lys Ile Ala Leu Lys Leu Val Gly Glu
            690                 695                 700
Glu Gly Phe Val Val Thr Glu Ala Gly Phe Ala Asp Ile Gly Met
705                 710                 715                 720
Glu Lys Phe Phe Asn Ile Lys Cys Arg Ala Ser Gly Leu Val Pro Asn
                725                 730                 735
Val Val Leu Val Ala Thr Val Arg Ala Leu Lys Met His Gly Gly
            740                 745                 750
Gly Pro Ser Val Thr Ala Gly Val Pro Leu Lys Lys Glu Tyr Thr Glu
            755                 760                 765
Glu Asn Ile Gln Leu Val Ala Asp Gly Cys Cys Asn Leu Gln Lys Gln
    770                 775                 780
Ile Gln Ile Thr Gln Leu Phe Gly Val Pro Val Val Ala Leu Asn
785                 790                 795                 800
Val Phe Lys Thr Asp Thr Arg Ala Glu Ile Asp Leu Val Cys Glu Leu
                805                 810                 815
Ala Lys Arg Ala Gly Ala Phe Asp Ala Val Pro Cys Tyr His Trp Ser
            820                 825                 830
Val Gly Gly Lys Gly Ser Val Asp Leu Ala Arg Ala Val Arg Glu Ala
            835                 840                 845
Ala Ser Lys Arg Ser Arg Phe Gln Phe Leu Tyr Asp Gln Val Pro
    850                 855                 860
Ile Val Asp Lys Ile Arg Thr Ile Ala Gln Ala Val Tyr Gly Ala Lys
865                 870                 875                 880
Asp Ile Glu Leu Ser Pro Glu Ala Gln Ala Lys Ile Asp Arg Tyr Thr
                885                 890                 895
Gln Gln Gly Phe Gly Asn Leu Pro Ile Cys Met Ala Lys Thr His Leu
            900                 905                 910
Ser Leu Ser His Gln Pro Asp Lys Lys Gly Val Pro Arg Asp Phe Ile
    915                 920                 925
Leu Pro Ile Ser Asp Val Arg Ala Ser Ile Gly Ala Gly Phe Ile Tyr
    930                 935                 940
Pro Leu Val Gly Thr Met Ser Thr Met Pro Gly Leu Pro Thr Arg Pro
945                 950                 955                 960
Cys Phe Tyr Asp Ile Asp Leu Asp Thr Glu Thr Glu Gln Val Lys Gly
                965                 970                 975
Leu Phe

<210> SEQ ID NO 3
<211> LENGTH: 38
<212> TYPE: DNA
<213> ORGANISM: Homo sapiens

<400> SEQUENCE: 3
cgggatccgc catgggcacg cgtctgccgc tcgtcctg                          38

<210> SEQ ID NO 4
<211> LENGTH: 38
<212> TYPE: DNA
<213> ORGANISM: Homo sapiens

<400> SEQUENCE: 4
ccgctcgagg aacaagcctt taacttgttc tgtttcgg                          38

<210> SEQ ID NO 5

```
<211> LENGTH: 23
<212> TYPE: DNA
<213> ORGANISM: Homo sapiens

<400> SEQUENCE: 5
gctttggtgc tgacatcgga atg                                              23

<210> SEQ ID NO 6
<211> LENGTH: 23
<212> TYPE: DNA
<213> ORGANISM: Homo sapiens

<400> SEQUENCE: 6
cccggacgtc actgataggt aag                                              23

<210> SEQ ID NO 7
<211> LENGTH: 5
<212> TYPE: PRT
<213> ORGANISM: Homo sapiens

<400> SEQUENCE: 7

Ser Ser Gly Gly Gly
1               5
```

TETRAHYDROFOLATE SYNTHETASE GENE

CROSS-REFERENCE TO RELATED APPLICATIONS

This is a divisional of application Ser. No. 10/573,969 filed Mar. 30, 2006 (now U.S. Pat. No. 7,534,562) which is a National Stage Application filed under §371 of PCT Application No. PCT/JP2004/014812 filed Sep. 30, 2004. The entire disclosures of the prior applications, are considered part of the disclosure and are hereby incorporated by reference.

TECHNICAL FIELD

This invention relates to a tetrahydrofolate synthetase gene, a DNA concerned in said gene and a protein encoded by said DNA. Also, it relates to a DNA which hybridizes with at least either one of a DNA comprising said DNA, a complementary chain of said DNA, a DNA represented by a partial nucleotide sequence of the DNA concerned in said gene and a complementary chain of said DNA. Further, it relates to a recombinant vector comprising the DNA concerned in said gene, a transformant comprising said vector, a method for producing said protein using said transformant and an antibody for said protein. Also, it relates to a method for identifying a compound which inhibits the cell growth accelerating activity possessed by said protein. Further, it relates to a method for judging whether or not a certain tissue is a colon cancer derived tissue. Also, it relates to a preventive agent and/or therapeutic agent for a cancer, which comprises an inhibitor of said protein. In addition, it relates to a kit for judgment of colon cancer, which comprises a DNA which hybridizes with at least either one of a DNA comprising the DNA concerned in said gene, a complementary chain of said DNA, a DNA represented by a partial nucleotide sequence of the DNA concerned in said gene and a complementary chain of said DNA and/or said antibody.

BACKGROUND OF THE INVENTION

Tetrahydrofolate synthetase (to be referred to as C1-THFS hereinafter) is an enzyme which synthesizes a tetrahydrofolic acid derivative that provides C1 group necessary for various metabolic reactions (Non-patent Reference 1; hereinafter, tetrahydrofolic acid is referred to as TF, and tetrahydrofolic acid derivative as TF derivative). Illustratively, TF derivatives give C1 group to the biosynthesis reactions of purine, thymidylic acid histidine, pantothenic acid and the like. That is, TF and TF derivatives are deeply concerned in nucleic acid metabolism, amino acid metabolism and the like. Thus, TF and TF derivatives are found in tissues where cell division is vigorously carried out and essential for cell multiplication and growth.

C1-THFS is a tri-functional enzyme which has 3 types of functions. Illustratively, C1-THFS has the functions of 10-formyl-THF synthetase (EC 6.3.4.3), 5,10-methenyl-THF cyclohydrolase (EC 3.5.4.9) and 5,10-methylene-THF dehydrogenase (EC 1.5.1.5). By exerting these functions, C1-THFS accelerates synthesis of TF derivatives which are necessary for various metabolic reactions.

Analysis of C1-THFS has been carried out using human, mouse, yeast and the like eucaryote, *Escherichia coli* and the like procaryote and the like various organism species as the object (Non-patent References 2 to 5). Regarding yeast, the presence of a C1-THFS which functions in its cytoplasm and mitochondria is known. Also, regarding human, the presence of a C1-THFS which functions in the cytoplasm of its cells is known.

However, the presence of a C1-THFS which functions in the mitochondria of human cells is not known, and there is only one report of Non-patent Reference 19. In addition, a human C1-THFS gene whose expression is elevated in colon cancer tissue in comparison with normal colon tissue is not known, too.

The references cited in this description are listed in the following.

Non-patent Reference 1
Hum D W et al., *The Journal of Biological Chemistry*, 1988, vol. 263, no. 31, pp. 15946-15950.

Non-patent Reference 2
Staben, C et al., *The Journal of Biological Chemistry*, 1984, vol. 261, pp. 4629-4637.

Non-patent Reference 3
Shannon, K. W. et al., *The Journal of Biological Chemistry*, 1986, vol. 261, pp. 12266-12271.

Non-patent Reference 4
Thigpen, A. E. et al., *The Journal of Biological Chemistry*, 1990, vol. 265, pp. 7907-7913.

Non-patent Reference 5
Dev, I. K. et al., *The Journal of Biological Chemistry*, 1978, vol. 253, pp. 4245-4253.

Non-patent Reference 6
Raj S K et al., *Biochemistry and Molecular Biology International*, vol. 44, no. 1, pp. 89-95.

Non-patent Reference 7
Frohman M. A. et al., *Proceedings of The National Academy of Science of The United States of America*, 1988, vol. 85, no. 23, pp. 8998-9002.

Non-patent Reference 8
*Proceedings of The National Academy of Science of The United States of America*, 1977, vol. 74, pp. 5463-5467.

Non-patent Reference 9
*Methods in Enzymology*, 1980, no. 65, p. 499-.

Non-patent Reference 10
Claros M G et al., *European Journal of Biochemistry*, 1996, vol. 241, no. 3, pp. 779-786.

Non-patent Reference 11
Kim P J et al., *Lancet*, 2003, vol. 362, pp. 205-209.

Non-patent Reference 12
R. H. Giles et al., *Biochimica et Biophysica Acta*, 2003, vol. 1653, pp. 1-24.

Non-patent Reference 13
He T C et al., *Science*, 1998, vol. 128, pp. 1509-1515.

Non-patent Reference 14
Levens D L, *Genes and Development*, 2003, no. 17, pp. 1071 1077.

Non-patent Reference 15
Garrow T A et al., *The Journal of Biological Chemistry*, 1993, vol. 268, pp. 11910-11916.

Non-patent Reference 16
Nikiforov M A et al., *Molecular and Cellular Biology*, 2002, vol. 22, pp. 5793-5800.

Non-patent Reference 17
Tavtigian S V et al., *Molecular Biology of the Cell*, 1994, vol. 5, pp. 375-388.

Non-patent Reference 18
Villar E, *The Journal of Biological Chemistry*, 1985, vol. 260, no. 4, pp. 2245-2252.

Non-patent Reference 19
Prasannan P et al., *The Journal of Biological Chemistry*, 2003, vol. 278, no. 44, pp. 43178-43187.

Non-patent Reference 20
Sugiura et al., *Biochemical and Biophysical Research Communications*, 2004, vol. 315, no. 1, pp. 204-211.

DISCLOSURE OF THE INVENTION

The problem that the invention is to solve is to find and provide a DNA concerned in a novel C1-THFS gene and a protein encoded by said DNA. Also, provision of a DNA which hybridizes with at least either one of a DNA comprising the DNA concerned in said gene, a complementary chain of said DNA, a DNA represented by a partial nucleotide sequence of the DNA concerned in said gene and a complementary chain of said DNA is also included in the problem. Further, provision of a recombinant vector comprising the DNA concerned in said gene, a transformant transformed using said vector, an antibody for said protein, a method for producing said protein and a method for identifying a compound which inhibits the cell growth accelerating activity of said protein is also included in the problem. Further, provision of a kit for judgment of colon cancer, which contains a DNA comprising the DNA concerned in said gene, a complementary chain of said DNA, a DNA represented by a partial nucleotide sequence of the DNA concerned in said gene and a complementary chain of said DNA and/or said antibody, and a method for judging whether or not a certain tissue is a colon cancer derived tissue is also included in the invention. In addition, provision of a preventive agent and/or therapeutic agent for colon cancer is also included in the problem.

The present inventors have conducted intensive efforts for the aforementioned problem and found a novel C1-THFS gene and succeeded in preparing a novel C1-THFS using a DNA concerned in said gene. Thereafter, by analyzing nucleotide sequence of said DNA, it was found that said C1-THFS transfers from cytoplasm to mitochondria and functions in mitochondria. Also, it was proved that said C1-THFS has a cell growth accelerating activity. In addition, it was proved that expression of said C1-THFS gene is significantly elevated in colon cancer tissue in comparison with that in normal colon tissue, thereby accomplishing the invention.

That is, the invention includes the following embodiments.

(1) A DNA of either one of the following (a) and (b):
(a) a DNA represented by a nucleotide sequence of from the 94th to 2934th positions of the nucleotide sequence described in SEQ ID NO:1 of the SEQUENCE LISTING,
(b) a DNA represented by the nucleotide sequence described in SEQ ID NO:1 of the SEQUENCE LISTING.

(2) A DNA which comprises the 94th to 2934th positions of the nucleotide sequence described in SEQ ID NO:1 of the SEQUENCE LISTING, and also encodes a protein having 3 activities of 10-formyl-tetrahydrofolate synthetase activity, 5,10-methenyl-tetrahydrofolate cyclohydrolase activity and 5,10-methylene-tetrahydrofolate dehydrogenase activity, and/or a cell growth accelerating activity.

(3) The DNA described in (2), which is a DNA represented by the nucleotide sequence described in SEQ ID NO:1 of the SEQUENCE LISTING.

(4) A DNA which comprises a nucleotide sequence wherein 1 or 2 or more of bases in the DNA sequence of the DNA described in any one of (1) to (3) are deleted, substituted or added, and encodes a protein having a cell growth accelerating activity.

(5) A DNA which hybridizes with at least either one of a DNA comprising the DNA described in any one of (1) to (4), a complementary chain of said DNA, a DNA represented by a partial nucleotide sequence of the DNA described in any one of (1) to (4) and a chain of said DNA, under a stringent condition.

(6) The DNA described in (5), which is a primer for amplifying at least one of a DNA comprising the DNA described in any one of (1) to (4), a complementary chain of said DNA, a DNA represented by a partial nucleotide sequence of the DNA described in any one of (1) to (4) and a chain of said DNA, and/or a probe for detecting the same, and is a DNA selected from the following group;
(i) a DNA represented by the nucleotide sequence described in SEQ ID NO:3 of the SEQUENCE LISTING,
(ii) a DNA represented by the nucleotide sequence described in SEQ ID NO:4 of the SEQUENCE LISTING,
(iii) a DNA represented by the nucleotide sequence described in SEQ ID NO:5 of the SEQUENCE LISTING, and
(iv) a DNA represented by the nucleotide sequence described in SEQ ID NO:6 of the SEQUENCE LISTING.

(7) A recombinant vector which comprises the DNA described in any one of (1) to (4).

(8) A plasmid FERM BP-8419.

(9) A transformant transformed with the recombinant vector described in (7) or the plasmid described in (8).

(10) A protein of either one of the following (a) and (b);
(a) a protein represented by an amino acid sequence of from the 32nd to 978th positions of the amino acid sequence described in SEQ ID NO:2 of the SEQUENCE LISTING,
(b) a protein represented by the amino acid sequence described in SEQ ID NO:2 of the SEQUENCE LISTING.

(11) A protein encoded by the DNA described in (4).

(12) A method for producing the protein described in (10) or (11), which comprises a step of culturing a transformant transformed with the recombinant vector described in (7) or the plasmid described in (8).

(13) An antibody for the protein described in (10) or (11) or a fragment of said protein as the antigen.

(14) A method for identifying a compound that inhibits the cell growth accelerating activity possessed by the protein described in (10) or (11), characterized in that whether or not a certain compound inhibits the cell growth accelerating activity of the protein described in (10) or (11) is judged by detecting the presence, absence or change of the cell growth accelerating activity under such a condition that interaction between said compound and the protein described in (10) or (11) is enabled.

(15) A method for identifying a compound that inhibits the cell growth accelerating activity possessed by the protein described in (10) or (11), characterized in that it uses at least one of the protein described in (10) or (11), the DNA described in any one of (1) to (4), the DNA described in (5) or (6), the recombinant vector described in (7) or the plasmid described in (8), the transformant described in (9) and the antibody described in (13).

(16) A method for judging whether or not a certain tissue is a colon cancer derived tissue, characterized in that expressed amount of the DNA described in any one of (1) to (4) in the certain tissue is measured.

(17) The judging method described in (16), wherein it is judged that a certain tissue is a colon cancer derived tissue when expressed amount of the DNA described in any one of (1) to (4) in the certain tissue is 3 times or more of the expressed amount of the DNA described in any one of (1) to (4) in a normal colon derived tissue as the control.

(18) The judging method described in (17), wherein expressed amount of the DNA described in any one of (1) to (4) in a certain tissue is measured by the following steps;
(i) a step for carrying out reverse transcription reaction using RNA contained in the certain tissue as the template,
(ii) a step for carrying out polymerase chain reaction using the cDNA synthesized by the reverse transcription reaction as the template, and DNA fragments represented by the nucleotide sequences described in SEQ ID NOs:5 and 6 of the SEQUENCE LISTING as the primers, and
(iii) a step for measuring amount of DNA amplified by the polymerase chain reaction.

(19) A colon cancer judging kit which is used in the judging method described in any one of (16) to (18), characterized in that it contains at least either one of the DNA described in (5) or (6) and the antibody described in (13).

(20) A preventive agent and/or therapeutic agent for colon cancer, which comprises an inhibitor of the protein described in (10) or (11).

ND represents N-terminal moiety DNA, NT represents N-terminal deficient DNA, and SP represents target sequence (signal peptide).

Figure 2:
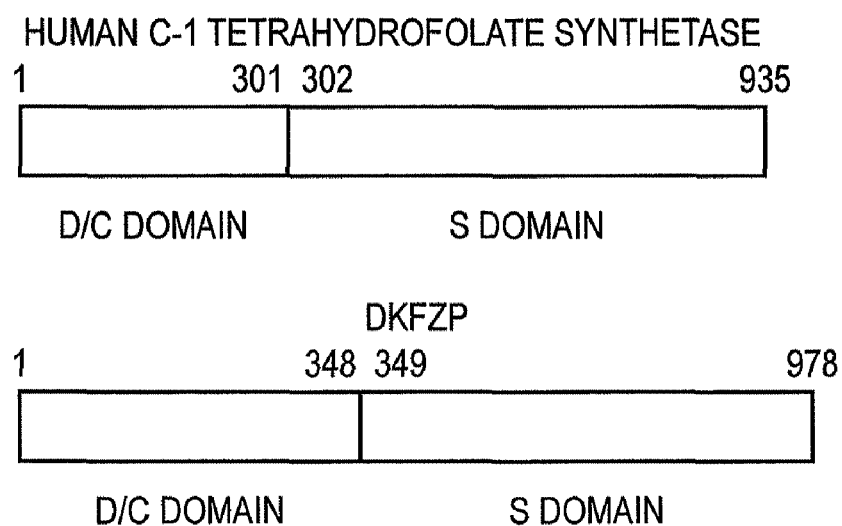

FIG. 2 is a view showing primary structures of human C1-THFS (human C-1 tetrahydrofolate synthetase) and the gene (DKFZP) concerned in the DNA to be provided by the invention. D/C domain means a partial structure which corresponds to the enzyme activity of 5,10-methenyl-tetrahydrofolate cyclohydrolase or 5,10-methylene-THF dehydrogenase. S domain means a partial structure which corresponds to the enzyme activity of 10-formyl-tetrahydrofolate synthetase.

Figure 3:
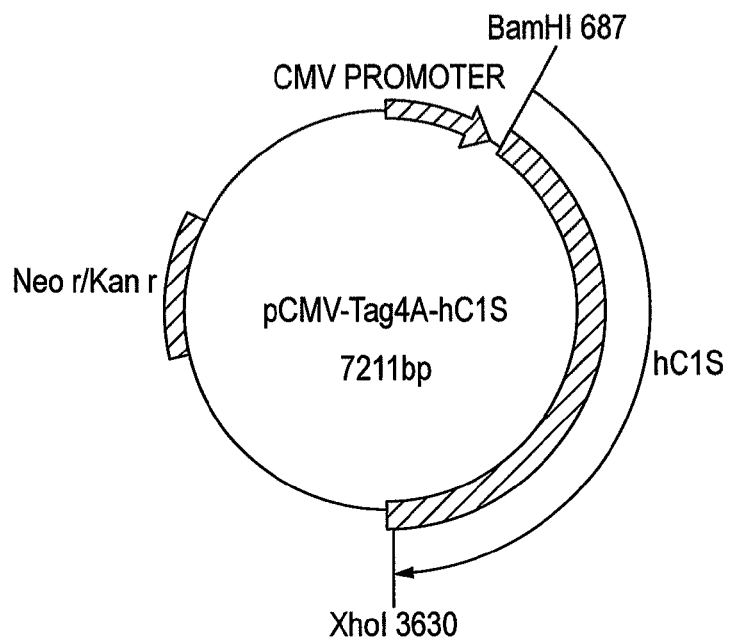

FIG. 3 is a drawing showing the structure of pCMV-Tag4A-hC1S. In the drawing, BamHI687 and XhoI3630 show recognition sites of restriction enzymes BamHI and XhoI. CMV promoter shows cytomegalovirus promoter region, and Neo r/Kan r show neomycin and kanamycin resistance gene region. The hC1S shows insertion region of the gene concerned in the DNA to be provided by the invention.

Figure 4:
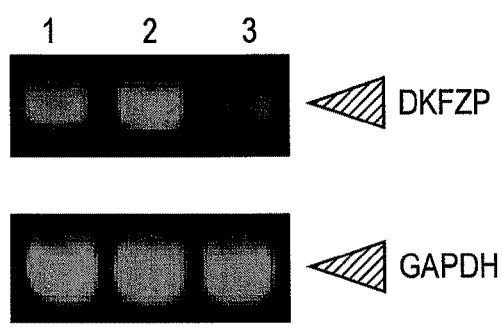

FIG. 4 is a photograph showing expression quantity of the gene concerned in the DNA to be provided by the invention in normal colon cell and colon cancer cell. Expression quantity of the gene concerned in the DNA to be provided by the invention is shown in the upper row, and expression quantity of glyceraldehyde 3-phosphate dehydrogenase as the control is shown in the lower row.

The numeral 1 represents a colon cancer cell HCT116, 2 represents a colon cancer cell SW620 and 3 represents a normal colon cell CCD841CoN. DKFZP shows expression quantity of the gene to be provided by the invention, and GAPDH shows expression quantity of glyceraldehyde 3-phosphate dehydrogenase.

Figure 5:
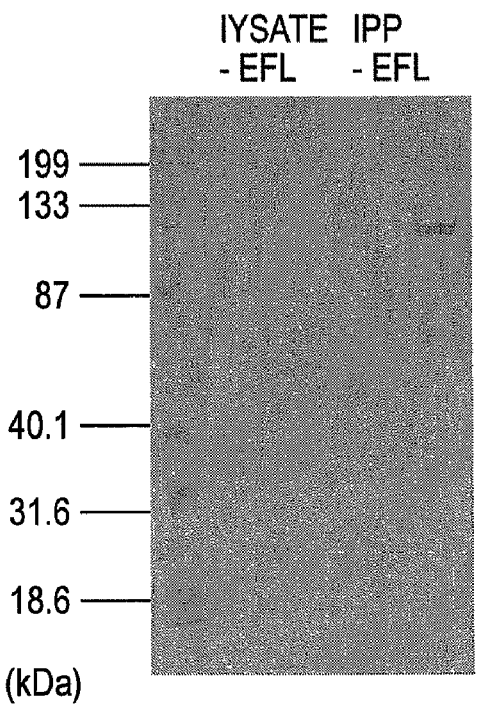

FIG. 5 is a photograph showing a result of western blotting verifying expression of protein encoded by the gene concerned in the DNA to be provided by the invention. In the drawing, lysate is a sample of 293 cell lysate, and IPP is a sample of the precipitate after immunoprecipitation in the 293 cell lysate with an anti-FLAG antibody.

The symbol — shows a sample derived from an animal cell of no gene transfer, E shows a sample derived from an animal cell in which pCMV-Tag4 vector was transferred, and FL shows a sample derived from an animal cell in which the recombinant pCMV-Tag4 vector concerned in the DNA to be provided by the invention was transferred.

Figure 6:
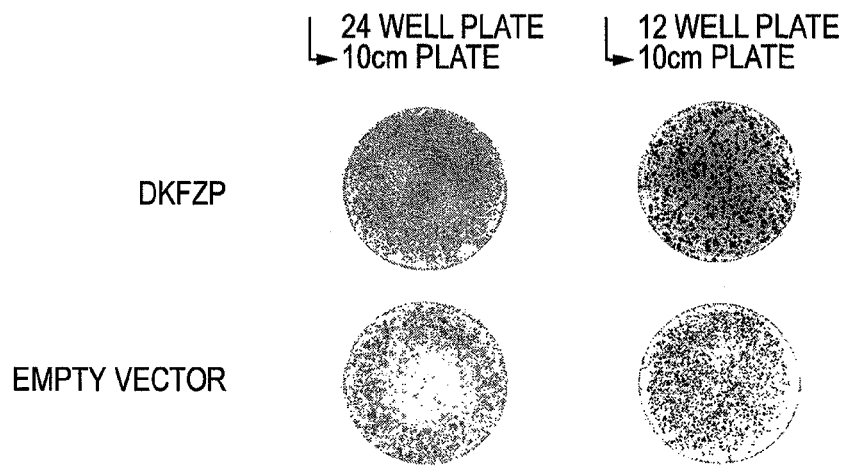

FIG. 6 is a photograph showing that a protein encoded by the gene concerned in the DNA to be provided by the invention accelerates cell growth. The 24 well plate→10 cm plate lane shows a sample in which the gene concerned in the DNA to be provided by the invention was transferred into 293 cell inoculated into a 24 well plate, and then the cell was again inoculated into a 10 cm plate. The 12 well plate→10 cm plate lane shows a sample in which the gene concerned in the DNA to be provided by the invention was transferred into 293 cell inoculated into a 12 well plate, and then the cell was again inoculated into a 10 cm plate.

DKFZP shows growth of an animal cell into which the recombinant pCMV-Tag4 vector concerned in the DNA to be provided by the invention was transferred, and Empty Vector shows growth of the animal cell into which pCMV-Tag4 vector was transferred.

Figure 7:
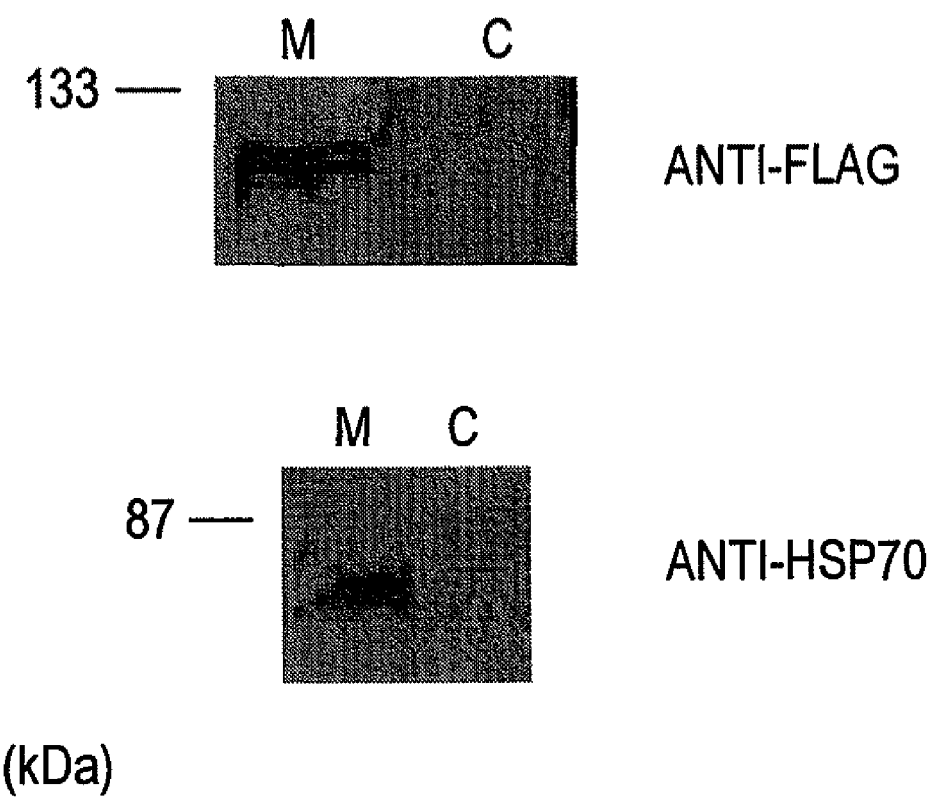

FIG. 7 is a photograph showing intracellular localization of the protein encoded by the gene concerned in the DNA to be provided by the invention. In the drawing, M shows a mitochondria fraction isolated from the 293 cell transferred with the gene concerned in the DNA to be provided by the invention, and C shows a cytoplasmic fraction thereof. The upper row shows a result of immunoblotting by an anti-FLAG, and the lower row shows a result by an anti-mitochondria HSP 70 antibody.

Figure 8:
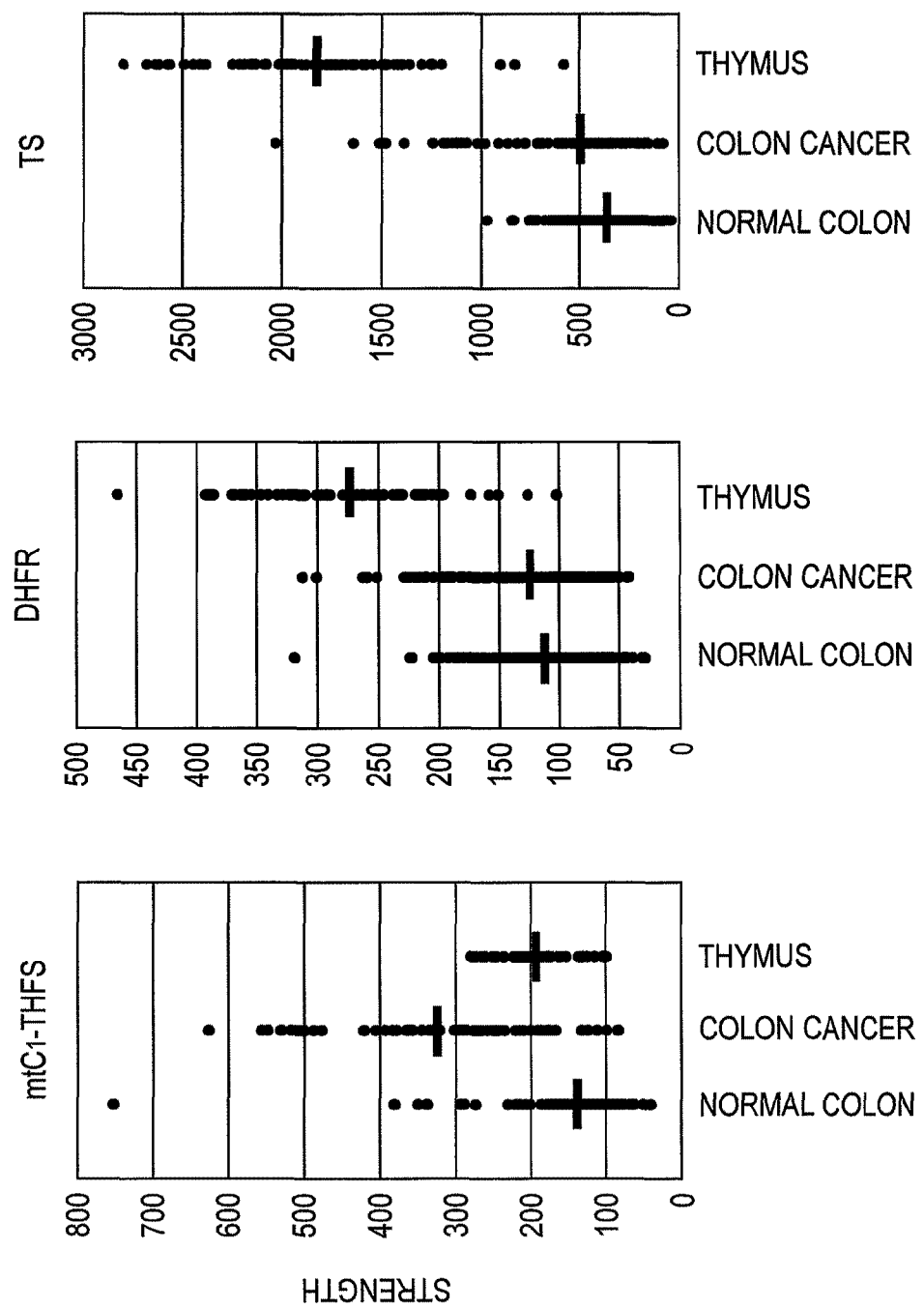

FIG. 8 is a graph showing comparison of expression patterns of existing antitumor agent target genes and the gene concerned in the DNA to be provided by the invention. The left side drawing is an expression pattern of the gene concerned in the DNA to be provided by the invention, and the middle drawing that of DHFR gene and the right side drawing that of TS gene, and expression strengths in normal colon tissue, colon cancer and thymus, starting from left, are shown in each drawing. Each dot shows the strength in each organ sample, and the bar shows their average value.

Figure 9:
Figure 9:
Figure 9:

FIG. 9 is a view showing a cascade hypothesis of mitochondria one carbon unit metabolism system activation. It shows that activation of C1 unit metabolism of mitochondria is induced starting from the activation of β catenin and through steps.

BEST MODE FOR CARRYING OUT THE INVENTION

According to this description, the "stringent condition" means, for example, a case in which a sample is heated at 42° C. in a solution of 6×SSC, 0.5% SDS and 50% formamide, and then washed at 68° C. in a solution of 0.1×SSC and 0.5% SDS.

The hybridization means a case in which it was carried out in accordance with the methods described in Molecular Cloning, A Laboratory Manual, edited by T. Maniatis et al., published in 1989 by Cold Spring Harbor Laboratory, and the like.

According to this description, the "homology" means a numerical value calculated, for example, using BLAST (National Center for Biotechnology Information).

According to this description, the "tissue" may contain one or more cells, and a single cell is also included in the definition of "tissue".

(Preparation of the Instant Gene)

The DNA concerned in the instant gene can be prepared making use of the conventionally known DNA cloning method, RT-PCR method (Non-patent Reference 6), RACE method (Non-patent Reference 7) and the like. For example, when the RT-PCR method is used, total RNA is extracted from an appropriate origin in which expression of the DNA concerned in the instant gene was confirmed, making use of a conventionally known RNA preparation method. Since expression of the instant gene is elevated in human colon cancer tissue in comparison with normal colon tissue, the human colon cancer tissue can be exemplified as said origin. Next, cDNA is synthesized from the extracted RNA making use of a conventionally known reverse transcriptase reaction. As primers for the reverse transcriptase reaction, oligo(dT)

primers, random primers and the like can be exemplified. These primers can be obtained by their synthesis in accordance with the usual way. The synthesized cDNA is amplified making use of a conventionally known PCR method using primers peculiar to the nucleotide sequence of cDNA (two primers of a sense primer and an antisense primer). The primers for PCR can be optionally designed based on the nucleotide sequence information of the cDNA, and can be obtained by synthesis in accordance with the usual way. As the sense primer, a DNA consisting of the DNA sequence described in SEQ ID NO:3 of the SEQUENCE LISTING can be exemplified. As the antisense primer, a DNA consisting of the DNA sequence described in SEQ ID NO:4 of the SEQUENCE LISTING can be exemplified. Isolation and purification of the amplified cDNA can be carried out in the usual way. For example, this can be carried out by a gel electrophoresis. After the amplification, the DNA concerned in the instant gene can be obtained as the isolated and purified cDNA.

Nucleotide sequence of the thus obtained DNA can be determined making use of conventionally known methods. For example, the nucleotide sequence can be determined making use of the dideoxy method (Non-patent Reference 8) or Maxam-Gilbert method (Non-patent Reference 9).

(Function of the Instant Gene)

It was revealed that the instant gene is a novel gene of ORF 2934 bp, coding for 978 amino acids. Of which, an amino acid sequence of from the 1st to 31st positions is the mitochondria target sequence, and a protein represented by an amino acid sequence of from 32nd to 678th positions is the mature protein.

Figure 1:
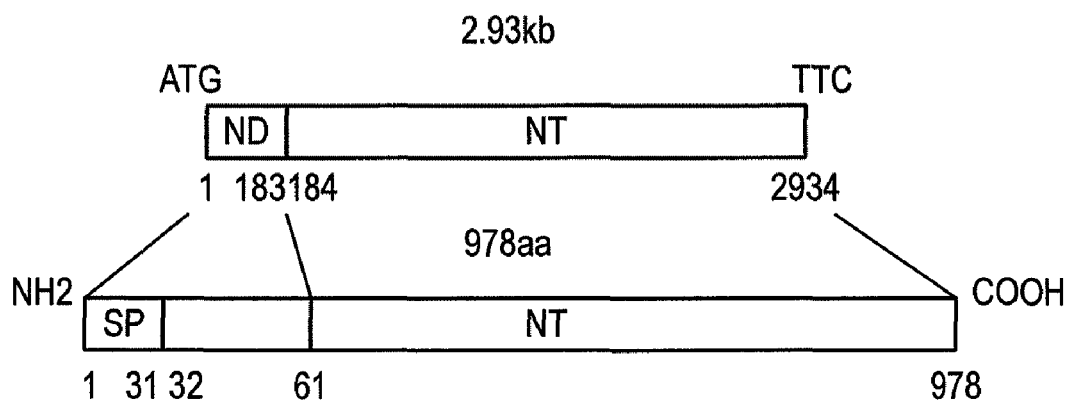
FIG. 1 is a view showing cDNA of the gene concerned in the DNA to be provided by the invention and primary structure of the protein encoded by said gene. The cDNA is shown in the upper row, and the protein primary structure in the lower row.

Nucleotide sequence of a DNA moiety (to be referred to as N-terminal deficient DNA) of the DNA concerned in the instant gene in which a part of the 5'-end moiety (to be referred to as N-terminal moiety DNA) was missed is registered on a nucleotide data base (DDBJ/EMBL/GenBank) and opened to the public (FIG. 1). It is known that the N-terminal deficient DNA has high homology on nucleotide sequence with the already known DNA concerned in human C1-THFS gene (FIG. 2).

As a result of homology retrieval of the N-terminal deficient DNA with the already known DNA concerned in human CL-THFS gene on their amino acid sequences, it was revealed that, among partial sequences on the already known human CL-THFS gene corresponding to the three types of enzyme activities possessed by the already known human CL-THFS gene, the N-terminal deficient DNA has a homology of about 75.7% with the partial sequence corresponding to the enzyme activity of 10-formyl-tetrahydrofolate synthetase, a homology of about 33.2% with the partial sequence corresponding to the enzyme activity of 5,10-methenyl-tetrahydrofolate cyclohydrolase, and a homology of about 33.2% with the partial sequence corresponding to the enzyme activity of 5,10-methylene-tetrahydrofolate dehydrogenase.

Also, a human CL-THFS ortholog has already been discovered. As a result of homology retrieval of the human C1-THFS ortholog gene with the already known human C1-THFS gene on their nucleotide sequences, it was found that, among partial sequences corresponding to the three types of enzyme activities possessed by the already known human C1-THFS gene, homology with the partial sequence corresponding to the enzyme activity of 10-formyl-tetrahydrofolate synthetase is high in comparison with the homology with the partial sequence corresponding to the enzyme activity of 5,10-methenyl-tetrahydrofolate cyclohydrolase and the partial sequence corresponding to the enzyme activity of 5,10-methylene-tetrahydrofolate dehydrogenase. In addition, it was revealed also that the protein encoded by the human C1-THFS ortholog gene has all of the three enzyme activities possessed by the already known human C1-THFS.

That is, it is considered that in comparison with the partial structure corresponding to the enzyme activity of 10-formyl-tetrahydrofolate synthetase, the partial structure corresponding to the enzyme activity of 5,10-methenyl-tetrahydrofolate cyclohydrolase and the partial structure corresponding to the enzyme activity of 5,10-methylene-tetrahydrofolate dehydrogenase are partial structures in which their activities are not easily lost by a change of amino acid sequence caused by a DNA mutation or the like.

Based on these, it is considered that the protein encoded by the DNA concerned in the instant gene also has all of the three enzyme activities possessed by C1-THFS. That is, it is considered that the protein encoded by the DNA concerned in the instant gene is an isozyme of the human C1-THFS.

On the other hand, those which have a specific target sequence in the N-terminal moiety are present among proteins synthesized on ribosome. It is known that these proteins are transferred to Golgi body, mitochondria and the like cell organelles by the target sequences. The target sequences possessed by all of the proteins to be transferred to mitochondria do not always have a consensus on amino acid sequences. However, it is known that the target sequences possessed by all of the proteins to be transferred to mitochondria commonly have high containing ratio of basic amino acids, and the target sequences are hydrophobic in general (Non-patent Reference 10). Accordingly, it is possible to predict whether or not an optional protein having distinct amino acid sequence has a target sequence for its transfer to mitochondria, using this tendency as the index.

As a result of predicting whether or not a polypeptide encoded by the N-terminal DNA has a target sequence, from its amino acid sequence, it was revealed that the polypeptide encoded by the N-terminal DNA has a target sequence. Accordingly, it is considered that the protein encoded by the DNA concerned in the instant gene is synthesized on ribosome and transferred to mitochondria, a peptide concerned in the target sequence is further cut off in mitochondria, and as a result, the polypeptide resulting from the removal of the peptide concerned in the target sequence functions as a mature protein. As shown in the following Examples, it was confirmed that an amino acid sequence of from 1st to 31st positions of the amino acid sequence of SEQ ID NO:2 is the mitochondria target sequence.

In addition, as a result of transferring the DNA concerned in the instant gene into a cell strain derived from human fetal kidney using liposome, growth of the cell was accelerated in comparison with the case of no transfer. Since it is predicted that the protein encoded by the DNA concerned in the instant gene has the three enzyme activities of C1-THFS, it is considered that the result of cell growth acceleration is due to concern of the protein encoded by the DNA concerned in the instant gene in the nucleic acid synthesis.

In comparison with the N-terminal deficient DNA, the DNA concerned in the instant gene has an N-terminal moiety DNA, namely a DNA comprising a DNA concerned in the target sequence for transferring from cytoplasm to mitochondria. This means that, different from the gene coding for the already known human C1-THFS which functions by presenting in cytoplasm, the instant gene is a gene coding for a mitochondria localizing human C1-THFS. Also, expression of the instant gene is significantly elevated in colon cancer tissue in comparison with normal colon tissue. Based on the above, the invention contributes to the further elucidation of metabolic reaction of C1-THFS. In addition, the instant gene can contribute to the development of a new antitumor agent as a gene coding for a protein targeting at the antitumor agent, which is not present for the conventional C1-THFS genes.

(DNA)

The DNA concerned in the invention is a DNA which comprises a DNA represented by a nucleotide sequence of from the 94th to 2934th positions of the nucleotide sequence described in SEQ ID NO:1 of the SEQUENCE LISTING, preferably a DNA represented by a nucleotide sequence of from the 94th to 2934th positions described in SEQ ID NO:1 of the SEQUENCE LISTING, or a DNA represented by the nucleotide sequence described in SEQ ID NO:1 of the SEQUENCE LISTING.

Also included in the DNA concerned in the invention is a DNA which comprises the 94th to 2934th positions of the nucleotide sequence of SEQ ID NO:1 of the SEQUENCE LISTING, and also encodes a protein having 3 activities of 10-formyl-tetrahydrofolate synthetase activity, 5,10-methenyl-tetrahydrofolate cyclohydrolase activity and 5,10-methylene-tetrahydrofolate dehydrogenase activity, and/or a cell growth accelerating activity, preferably a DNA represented by a nucleotide sequence of from the 94th to 2934th positions described in SEQ ID NO:1 of the SEQUENCE LISTING, or a DNA represented by the nucleotide sequence described in SEQ ID NO:1 of the SEQUENCE LISTING.

In addition, a DNA which comprises the DNA sequence of the aforementioned DNA, wherein it has deletion, substitution, addition or the like mutation or induced mutation of 1 or 2 or more of bases, and encodes a protein having a cell growth accelerating activity, is also included in the DNA concerned in the invention. Said DNA may be a naturally occurring one, or a DNA obtained by introducing a mutation based on a natural origin gene. The method for introducing mutation is conventionally known, and a method for preparing deletion mutants using an exonuclease, a site-directed mutagenesis method and the like can be exemplified.

The "1 or 2 or more" is generally from 1 to 20, preferably from 1 to 10, more preferably from 1 to several. The several is generally from 1 to 5, preferably from 1 to 3, more preferably 1 or 2.

According to this description, the aforementioned DNA is called the DNA concerned in the instant gene.

In addition, a DNA which hybridizes with at least one of a DNA comprising the DNA concerned in the instant gene, a complementary chain of said DNA, a DNA represented by a partial nucleotide sequence of the DNA concerned in the instant gene and complementary chains of said DNA, under a stringent condition, is also included in the DNA concerned in the instant invention. Said DNA is a DNA consisting of preferably 5 or more nucleotides, more preferably 10 or more nucleotides, further preferably 20 or more nucleotides, as its minimum unit. It is desirable that said DNA has a nucleotide sequence region specific to the DNA concerned in the invention. It is possible to produce said DNA making use of a conventionally known chemical synthesis method (cf. *Gene*, vol. 60 (1), pp. 115-127 (1987)) based on the nucleotide sequence information of said DNA. Said DNA is used as a primer for amplifying the DNA concerned in the instant gene, a probe for detecting the DNA concerned in the instant gene and the like.

As the DNA comprising the DNA concerned in the instant gene, a DNA which has an additional sequence on the N-terminus and/or C-terminus of the DNA concerned in the instant gene can be exemplified. The additional sequences are not limited with the proviso that the protein encoded by such a DNA has cell growth activity and/or the aforementioned three enzyme activities.

In addition, a DNA which is a primer for amplifying at least one of a DNA comprising the DNA concerned in the instant gene, a complementary chain of said DNA, a DNA represented by a partial nucleotide sequence of the DNA concerned in the instant gene and complementary chains of said DNA, and/or a probe for detecting the same, is also included in the DNA concerned in the instant gene. Said DNA is used for the preparation of the instant gene, measurement of the amount of transcription products of the instant gene and the like. For example, said DNA is a DNA consisting of the nucleotide sequence described in any one of SEQ ID NOs:3 to 6 of the SEQUENCE LISTING. For example, a DNA consisting of the nucleotide sequence described in SEQ ID NO:3 or 4 of the SEQUENCE LISTING is used as a primer for amplifying a DNA comprising the DNA concerned in the instant gene and complementary chains of said DNA in preparing the DNA concerned in the instant gene. For example, a DNA consisting of the nucleotide sequence described in SEQ ID NO:5 or 6 of the SEQUENCE LISTING is used as a primer for amplifying a fragment of the DNA concerned in the instant gene and complementary chains of said DNA fragment and as a probe for detecting the DNA concerned in the instant gene and complementary chains of said DNA.

According to this description, DNA preparations among the aforementioned DNA preparations excluding the DNA preparations concerned in the instant gene are called DNA preparations which hybridize with the instant gene and the like.

(Protein)

An embodiment of the invention is a protein represented by an amino acid sequence of from 32nd to 978th positions of the amino acid sequence described in SEQ ID NO:2 of the SEQUENCE LISTING or a protein represented by the amino acid sequence described in SEQ ID NO:2 of the SEQUENCE LISTING. In addition, a protein encoded by the DNA concerned in the instant gene, such as a protein encoded by a DNA which has deletion, substitution, addition or the like mutation or induced mutation of 1 or 2 or more of bases in the DNA sequence of the DNA represented by the nucleotide sequence described in SEQ ID NO:1 of the SEQUENCE LISTING, and has a cell growth accelerating activity, is also included in the protein concerned in the invention.

It is possible to modify these proteins to such a degree that significant alteration of their functions does not occur, such as modification of the constituting amino group, carboxyl group or the like. For example, a protein labeled by adding other protein or the like to the N-terminus or C-terminus directly or indirectly via a linker protein using a genetic engineering technique or the like is also included in the invention. As the protein or the like to be added, glutathione S-transferase, β-galactosidase, alkaline phosphatase and the like enzymes, His-tag, Myc-tag, HA-tag, FLAG-tag and the like tag peptides, fluorescein isothiocyanate and the like fluorescent materials and the like can for example be cited. By the addition of these proteins or the like, it becomes possible to easily purify and detect the protein concerned in the invention.

The protein to be provided by the invention may be prepared from a cell in which a DNA coding for said protein is expressed by a genetic engineering technique, a cell-free system synthesis product, a chemical synthesis product or a biological sample derived from a living body, or may be the one further purified therefrom.

The protein to be provided by the invention is useful in carrying out screening of an inhibitor which inhibits the activity of said protein. For example, a cell growth accelerating activity can be cited as the activity of said protein.

By accomplishing the invention which provides the instant gene, the protein encoded by the DNA concerned in the instant gene can be expressed while keeping its C1-THFS activity. In addition, it also renders possible purification of said protein and screening of an agent targeting at said protein.

On the other hand, in comparison with an N-terminal deficient DNA, the DNA concerned in the instant gene is possessed of an N-terminal moiety DNA, namely a DNA concerned in the target sequence for transferring from cytoplasm to mitochondria, and a DNA represented by a partial nucleotide sequence of the DNA concerned in the structural gene. Accordingly, provided that the N-terminal deficient DNA is forcedly expressed in an animal cell or the like using an N-terminal deficient DNA, the N-terminal deficient DNA does not contain whole DNA concerned in the structural gene, so that it is considered that the expressed protein does not show the C1-THFS activity. In addition, since the N-terminal deficient DNA does not have the DNA concerned in the target sequence for transferring from cytoplasm to mitochondria, it can be hardly considered that the expressed protein is transferred from cytoplasm to mitochondria and shows the C1-THFS activity thereon.

(Recombinant Vector)

As one of the embodiments, the invention provides a recombinant vector which comprises the DNA concerned in the instant gene. The recombinant vector can be obtained by inserting the DNA concerned in the instant gene and the like into an appropriate vector DNA.

The vector DNA is optionally selected depending on the kind of transfected cell and the like. In addition to the one prepared by extracting naturally existing counterpart, the vector DNA may be another one in which a DNA moiety other than the moiety necessary for replication is partially deleted. For example, vectors derived from a plasmid, a bacteriophage and a virus can be cited. As the plasmid DNA, an *Escherichia coli* derived plasmid, a *Bacillus subtilis* derived plasmid and a yeast derived plasmid can be exemplified. As the bacteriophage DNA, λ phage and the like can be exemplified. As the virus derived vector DNA, retrovirus, vaccinia virus, adenovirus, papovavirus, SV40, baculovirus and the like can be exemplified. In addition to these, transposon derived, insertion element derived vector DNA and the like can be exemplified. Alternatively, a vector DNA prepared by a combination thereof (cosmid or the like) can be exemplified. The recombinant vector uses the gene sequence of interest and a gene sequence which carries information on the replication and control, such as a promoter, a ribosome binding region, a terminator, a signal sequence, an enhancer, a selection marker or the like, as the composing elements, and is prepared by combining them based on a conventionally known method. As the selection marker, an ampicillin resistance gene, a neomycin resistance gene and the like can be exemplified.

As the method for integrating a gene of interest into a vector DNA, a conventionally known method can be employed. For example, a method in which the gene of interest is digested at a specified site by selecting an appropriate restriction enzyme and treating therewith, subsequently mixed with a DNA to be used as the vector after treating in the same manner, and then connected again by a ligase. Alternatively, a desired vector can also be obtained by ligating an appropriate linker to the gene of interest, and inserting this into a multi-cloning site of a vector suited for the purpose.

In the pCMV-Tag4A-hC1S (FIG. 3) shown in the Examples which are described later, pCMV-Tag4 (mfd. by STRATAGENE) was used as the vector DNA. The pCMV-Tag4A-hC1S has been deposited on Jun. 25, 2003, as FERM BP-8419 in International Patent Organism Depositary, National Institute of Advanced Industrial Science and Technology (postal code 305-8566; Central 6, 1-1-1 Higashi, Tsukuba, Ibaraki). The plasmid FERM BP-8419 is also included in the invention.

(Transformant)

In one of the embodiments of the invention, a transformant obtained by introducing a recombinant vector concerned in the invention into a host is provided. When an expression vector is used as the vector DNA, the protein concerned in the invention can be provided. One or two or more of vector DNA into which a desired gene other than the DNA concerned in the invention is inserted can be further introduced into said transformant. The vector DNA to be introduced into a host may be one kind of vector or two or more kinds of vector DNA.

As the host, both of procaryote and eucaryote can be used. As the procaryote, *Escherichia coli*, *Bacillus subtilis* and the like can be exemplified. As the eucaryote, a yeast cell and an insect cell, or a monkey kidney derived cell, a Chinese hamster ovary cell, a mouse L cell, a rat GH3 cell, a human FL cell, a 293 EBNA cell and the like animal cells can be exemplified. Preferably, an animal cell is used. More preferably, a human cell is used.

The transformation can be carried out making use of a conventionally known method. Preferably, an integration method into chromosome of the host can be exemplified taking stability of the gene into consideration, but conveniently, an autonomous replication system using an extranuclear gene is used. Introduction of the DNA to be provided by the invention is carried out making use of a conventionally known method. For example, the calcium phosphate method, the electroporation method and the lipofection method can be cited, though not limited to these methods. From the viewpoints of introducing efficiency and convenience, the lipofection method can be preferably exemplified. In this connection, in the Examples which are described later, the protein concerned in the invention was expressed using a transformant obtained as a result of carrying out transformation by introducing pCMV-Tag4A-hC1S into a 293 cell by the lipofection method. The 293 cell means a human fetal kidney cell transformed with an oncogene E1 of adenovirus type 5.

(Production Method of Protein)

As one of the embodiments of the invention, there is provided a method for producing the protein concerned in the invention, which comprises a step for culturing the transformant concerned in the invention. Expression of the protein concerned in the invention can be carried out using a cell-free protein expression system. In addition to this, the protein concerned in the invention can be expressed using a gene recombination technique making use of an *Escherichia coli* cell, a yeast cell, a *Bacillus subtilis* cell, an insect cell, an animal cell or the like conventionally known host. For example, the protein concerned in the invention can be produced by culturing the transformant concerned in the invention, and subsequently recovering the protein of interest from a cultured material obtained by the culturing. Culturing of the transformant concerned in the invention can be carried out making use of conventionally known culture condition and culturing method most suited for each host. The culturing can be carried out using the cell growth accelerating activity of said protein expressed by the transformant as the index. In addition, this can also be carried out using the aforementioned 3 enzyme activities possessed by said protein as the index. These enzyme activities can be measured using a conventionally known method (Non-patent Reference 18). Alternatively, amount of said protein produced in the host or outside the host may be used as the index. The expressed protein can be purified and recovered making use of a conventionally known purification method. For example, it can be purified and recovered by a combination of molecular sieve, ion exchange chromatography, affinity chromatography and the like. In addition to this, it can also be purified and recovered by ammonium sulfate, alcohol and the like fractionation means. Preferably, it can be purified and recovered by preparing an antibody for the protein concerned in the invention, and making use of the specific adsorption of the protein concerned in the invention to said antibody.

(Antibody)

As one of the embodiments of the invention, an antibody for the protein concerned in the invention is provided. The antibody is prepared using the protein concerned in the invention or a fragment thereof as the antigen. The antigen may be either said protein or a fragment thereof and is constituted from at least 8, preferably at least 10, more preferably at least 12, more preferably 15 or more, of amino acids. In order to prepare an antibody specific for said protein, it is desirable to use a region consisting of an amino acid sequence peculiar to said protein and/or a fragment thereof. The amino acid sequence of this region is not necessarily the same as or homologous to the amino acid sequence concerned in the protein of the invention or a fragment thereof, but may be a region exposed to the outside of said protein in view of its three-dimensional structure, and even when the amino acid sequence of the exposed region is discontinued in view of its primary structure, it may be a continuous amino acid sequence regarding the exposed region. The antibody is not particularly limited with the proviso that it specifically binds to or recognizes the protein to be provided by the invention and/or a fragment thereof. The presence or absence of this binding or recognition can be determined making use of a conventionally known antigen-antibody binding reaction.

The antibody is produced making use of a conventionally known antibody preparation method. In order to produce the antibody, the protein to be provided by the invention or a fragment thereof is administered to an animal directly or by linking to a carrier, in the presence or absence of an adjuvant, to carry out humoral response and/or cellular response and the like immune induction in the animal. The carrier is not particularly limited with the proviso that it does not cause an injurious action upon the host and reinforces antigenicity, and for example, cellulose, polymerized amino acid, albumin and the like can be exemplified. As the animal to be immunized, mouse, rat, rabbit, goat, horse and the like are suitably used. A polyclonal antibody is prepared from serum of the aforementioned immunized animal making use of a conventionally known antibody recovering method. As a desirable antibody recovering method, an immune affinity chromatography can be exemplified.

Production of a monoclonal antibody is carried out by recovering an antibody producing cell (e.g., lymphocyte derived from the spleen or lymph node) from the aforementioned immunized animal, and employing a transformation means to a conventionally known persistently growing cell. For example, hybridomas are prepared by fusing the antibody producing cell and persistently growing cell by a conventionally known method and after cloned, a hybridoma capable of producing an antibody which specifically recognizes the protein to be provided by the invention and/or a fragment thereof is selected, and the antibody is recovered from a culture medium of said hybridoma.

The thus obtained polyclonal antibody or monoclonal antibody can be used directly as an antibody for purification, labeling marker and the like of the protein to be provided by the invention. In addition, said polyclonal antibody or said monoclonal antibody can control activity of the protein to be provided by the invention by binding thereto. Accordingly, this is useful for the treatment and/or prevention of a disease in which activity of the protein concerned in the invention is concerned. For example, since expression of the DNA concerned in the instant gene is elevated in human colon cancer tissue in comparison with human normal colon tissue, said polyclonal antibody or said monoclonal antibody is useful for the treatment and/or prevention of colon cancer. In addition, said polyclonal antibody or said monoclonal antibody can provide a colon cancer diagnosing means as a labeling marker of said protein.

(Identification Method of Compound)

As one of the embodiments of the invention, there is provided a method for identifying a compound which inhibits the cell growth accelerating activity of the protein concerned in the invention. Said compound identification method can be carried out making use of a conventionally known medicament screening system, using at least any one of the protein concerned in the invention, the DNA concerned in the invention, the recombinant vector concerned in the invention or the plasmid concerned in the invention, the transformant concerned in the invention and the antibody concerned in the invention. The identification method concerned in the invention renders possible selection of an antagonist by a drug design based on the three-dimensional structure of said protein, selection of an antibody recognizing substance making use of said antibody and the like. The compound identified by said identification method is useful for the treatment and/or prevention of a disease in which activity of the protein concerned in the invention is concerned. Expression of the DNA concerned in the instant gene is elevated in human colon cancer tissue in comparison with human normal colon tissue. Accordingly, said compound is useful for the treatment and/or prevention of colon cancer.

For example, in an experimental system for measuring cell growth accelerating activity of the protein concerned in the invention, said activity is measured by allowing said protein and a compound to be tested to coexist under a condition which renders possible interaction between said protein and the compound to be tested. Subsequently, it becomes possible to identify a compound which inhibits said activity of said protein by detecting the presence, absence or change of said activity, such as decrease, increase, disappearance, appearance and the like of the same, obtained based on the comparison with a result measured in the absence of the compound to be tested. Measurement of the activity can be carried out by direct detection or can be carried out, for example, by introducing a signal to be used as the index of the activity into the experimental system and then detecting said signal. As the signal, glutathione S-transferase, or His-tag, Myc-tag, HA-tag, FLAG-tag and the like tag peptides and the like can be used.

By comparing said activity of said protein in the case of the coexistence of a compound to be tested with said activity of said protein in the case of the absence of the compound to be tested, effect of said compound to be tested on said activity can be measured. When said activity in the case of the coexistence of said compound to be tested is reduced in comparison with said activity of said protein in the case of the absence of said compound to be tested, it can be judged that said compound to be tested has the effect to inhibit the activity of said protein.

As an example, by using the cell growth accelerating activity of the protein concerned in the invention as the index, a compound capable of giving influence upon said activity can be selected. Said cell growth accelerating activity can be determined by culturing a cell which expresses the protein concerned in the invention and counting the number of grown cells after the culturing. The number of cells can be counted by staining the intact cells using Violet, Neutral Red or the like. In addition, it is possible also to count the number of cells using incorporation of radiation-labeled thymidine by intact cells as the index.

(Judging Method of Colon Cancer)

Also, as one of the embodiments of the invention, there is provided a method for judging whether or not a certain tissue is a colon cancer derived tissue, characterized in that expressed amount of the DNA concerned in the instant gene in the certain tissue is measured. That is, expression of the DNA concerned in the instant gene is significantly elevated in colon cancer tissue in comparison with normal colon tissue. Accordingly, it is possible to judge whether or not a certain tissue is a colon cancer derived tissue, using expressed amount expression of the DNA concerned in the instant gene as the index.

Regarding the sample to be tested, it is not particularly limited with the proviso that it contains the gene to be provided by the invention and/or a nucleic acid of a mutant gene thereof and/or a nucleic acid fragment thereof. For example, colon tissue, colon tissue biopsy and the like living body derived biological samples can be exemplified as the sample to be tested. As the nucleic acid, a DNA comprising the DNA concerned in the instant gene, a complementary chain of said DNA, a fragment of the DNA concerned in the instant gene, a complementary chain of said DNA fragment, an RNA as a product of transcription of such a DNA and the like can be exemplified. The sample to be tested can be prepared using various methods which facilitate detection of nucleic acid contained in the sample, such as denaturation, restriction enzyme digestion, electrophoresis, dot blotting and the like methods.

Detection of said nucleic acid and measurement of the amount of said nucleic acid can be carried out making use of conventionally known gene detection method and measuring method. As said detection method, for example, in situ hybridization, northern blot technique and the like can be exemplified. As said measuring method, northern blot technique, quantitative RT-PCR, spectroscopic analysis and the like can be exemplified. For example, it is possible to measure expressed amount of the DNA concerned in the instant gene by the following steps.

(i) A step for carrying out reverse transcription reaction using RNA contained in a certain tissue as the template,
(ii) a step for carrying out polymerase chain reaction using the cDNA synthesized by the reverse transcription reaction as the template, and DNA fragments represented by the nucleotide sequences described in SEQ ID NOs:5 and 6 of the SEQUENCE LISTING as the primers, and
(iii) a step for measuring amount of DNA amplified by the polymerase chain reaction.

According to said detection method, the DNA concerned in the instant gene or a fragment of complementary chain of said DNA having a property as a probe or having a property as a primer is useful in carrying out identification of a gene concerned in the invention or a mutant gene thereof and/or amplification of a DNA concerned in said gene. The DNA fragment having a property as a probe means a DNA which can specifically hybridize only with the DNA concerned in the instant gene. The one having a property as a primer means a DNA which can specifically amplify only the DNA concerned in the instant gene. As the probe or primer, the one having a nucleotide sequence length of generally from about 5 to 50 nucleotides is preferable, the one having from about 10 to 35 nucleotides is more preferable, and the one having from about 15 to 30 nucleotides is further preferable. In general, labeled one is used as the probe, but it may be a non-labeled one. As a suitable label, a radioisotope, biotin, a fluorescent substance, a chemiluminescent substance, an enzyme, an antibody and the like can be exemplified. As the method for labeling a probe, nick translation, random priming, a method which uses kinase treatment and the like can be exemplified. For example, the polynucleotide concerned in the invention can be exemplified as said probe and/or primer.

In addition, when the expressed amount in the aforementioned identification method is 2 times or more, preferably 3 times or more, more preferably 4 times or more, further preferably 8 times or more, in comparison with the expressed amount of the DNA concerned in the instant gene in normal colon derived tissue as the control, it is possible to judge that the certain tissue is a colon cancer derived tissue. In the Examples which are described later, the expressed amount of said DNA in a colon cancer cell was about 2.38 times of the expressed amount of said DNA in a normal colon cell.

(Judging Kit of Colon Cancer)

Also, as one of the embodiments of the invention, there is provided a kit for judging colon cancer, characterized in that it contains at least either one of the DNA which hybridizes with the instant gene and the like and the antibody concerned in the invention. For example, since elevation of expression of the DNA concerned in the instant gene is found in human colon cancer tissue in comparison with human normal colon tissue, it is possible to judge whether or not a certain tissue is a colon cancer derived tissue, by detecting expressed product of said DNA in a tissue to be tested using the DNA contained in the colon cancer judging kit concerned in the invention as the probe and measuring expressed amount of said DNA. Said judging kit may contain a buffer solution, a salt, a stabilizing agent and/or an antiseptic and the like substances. In this connection, in preparing a pharmaceutical preparation, a conventionally known preparation means may be introduced according to the properties of the DNA which hybridizes with the instant gene and the like and said antibody.

(Preventing Agent and/or Therapeutic Agent for Colon Cancer)

As one of the embodiments, the invention provides a preventive agent and/or therapeutic agent for colon cancer, which comprises an inhibitor of the protein concerned in the invention. As the inhibitor of the protein concerned in the invention, an antibody concerned in the invention and a compound identified by the identification method concerned in the invention can be exemplified. Since expression of the DNA concerned in the instant gene is elevated in colon cancer tissue in comparison with normal colon tissue, inhibitor of the protein concerned in the invention is useful in preventing and/or treating colon cancer.

It is desirable to use 1 or 2 or more carriers for medicament use for the production of a medicament. Amount of the active ingredient to be contained in the pharmaceutical preparation concerned in the invention is optionally selected from a broad range, but it is appropriate to set it within the range of generally from about 0.00001 to 70% by weight, preferably from 0.0001 to 5% by weight.

As the carrier for medicament use, a bulking agent, an extending agent, a binder, a moistening agent, a disintegrating agent, a surfactant, a lubricant and the like diluents, fillers and the like, which are generally used according to the using form of the pharmaceutical preparations, can be exemplified, and these are optionally selected according to the administration form of the pharmaceutical preparation to be obtained.

For example, water, pharmaceutically acceptable organic solvent, collagen, polyvinyl alcohol, polyvinyl pyrrolidone, carboxy vinyl polymer, sodium alginate, water-soluble dextran, carboxymethyl starch sodium, pectin, xanthan gum, gum arabic, casein, gelatin, agar, glycerol, propylene glycol, polyethylene glycol, vaseline, paraffin, stearyl alcohol, stearic acid, human serum albumin, mannitol, sorbitol, lactose and the like can be cited. These are optionally used alone or as a combination of 2 or more according to the dosage forms concerned in the invention.

As occasion demands, the medicament can also be prepared by optionally using various components which are used in general pharmaceutical preparations, such as a stabilizing agent, a germicide, a buffer agent, a tonicity agent, a chelating agent, a pH adjusting agent, a surfactant.

As the stabilizing agent, for example, human serum albumin and general L-amino acid, saccharides, cellulose derivatives and the like can be exemplified, and these can be used alone or in combination with a surfactant or the like. Particularly according to this combination, stability of the active ingredient is further improved in certain cases. The aforementioned L-amino acid is not particularly limited, and it may be any one of for example glycine, cysteine, glutamic acid and the like. The saccharides are not particularly limited too, and for example they may be any one of glucose, mannose, galactose, fructose and the like monosaccharides, mannitol, inositol, xylitol and the like sugar alcohols, sucrose, maltose, lactose and the like disaccharides, dextran, hydroxypropyl starch, chondroitin sulfate, hyaluronic acid and the like polysaccharides and the like and derivatives thereof and the like. The cellulose derivatives are not particularly limited too, and they may be any one of methyl cellulose, ethyl cellulose, hydroxyethyl cellulose, hydroxypropyl cellulose, hydroxypropylmethyl cellulose and the like. The surfactant is not particularly limited too, and any one of ionic and anionic surfactants can be used. A polyoxyethylene glycol sorbitan alkyl ester system, a polyoxyethylene alkyl ether system, a sorbitan monoacyl ester system, a fatty acid glyceride system and the like are included therein.

As the buffer agent, boric acid, phosphoric acid, acetic acid, citric acid, $\epsilon$-amino-caproic acid, glutamic acid and/or salts corresponding thereto (e.g., their sodium salt, potassium salt, calcium salt, magnesium salt and the like alkali metal salts and alkaline earth metal salts) and the like can be exemplified.

As the tonicity agent, for example, sodium chloride, potassium chloride, saccharides, glycerol and the like can be exemplified.

As the chelating agent, for example, sodium edetate, citric acid and the like can be exemplified.

The medicament and pharmaceutical composition concerned in the invention can be used as a solution preparation and also can be used by making this into such a state that it can be freeze-dried, and then, when used, adjusting to an appropriate concentration by dissolving in water or a buffer solution containing physiological saline or the like.

The range of dose of the pharmaceutical composition is not particularly limited, and it is desirable to select it optionally, depending on the efficacy of the pharmaceutical composition of the invention, administration form, kind of the disease, properties of each object (body weight, age, the condition of the disease and the presence or absence of the use of other medicaments and the like) and judgment of the doctor in charge.

In general, it is desirable that the appropriate dose is within the range of for example from about 0.01 μg to about 100 mg, preferably from about 0.1 μg to about 1 mg, per 1 kg body weight of the object. However, change of these doses can be carried out using a general conventional test for optimization, which is well known in said field. The aforementioned dose can be administered by dividing it into one to several doses per day, or may be administered intermittently at a ratio of once per several days or several weeks.

A formula suited for each administration form may be selected, and said formula may be used by selecting a counterpart well known to those skilled in the art. In addition, when formulated, these may be used alone, or may be used together with other compound or medicament necessary for the treatment. For example, the active ingredient and the like of other medicament for antitumor use may be blended.

Regarding the administration form, either one of systemic administration and local administration can be selected. In this case, an appropriate administration form is selected according to the disease, symptom and the like. For example, in addition to the general intravenous administration and intraarterial administration, subcutaneous, intracutaneous, intramuscular and the like administrations can also be carried out. It can also be administered directly into a colon cancer tissue.

Shape of the medicament can be selected according to the administration form, and gene therapy agents, cyclodextrin and the like inclusion bodies, solutions, suspensions, fat emulsions, powders, ointments, creams, percutaneous absorption preparations, transmucosal absorption preparations, pills, tablets, capsules, granules, fine subtilaes, suppositories, inhalations, eye lotions, ear lotions and the like can also be prepared. However, embodiments of the medicament of the invention are not limited thereto.

In preparing pharmaceutical preparations, appropriate additives for pharmaceutical preparation use can be used according to the embodiment, and can be made into pharmaceutical preparations in accordance with the usual way.

Liposome formation can be carried out, for example, by adding a solution prepared by dissolving the substance of interest in a solvent to a solution prepared by dissolving phospholipid in an organic solvent (chloroform or the like), evaporating the solvent, adding phosphate buffer to the residue to carry out shaking, ultrasonic treatment and centrifugation treatment, and then filtering and recovering the supernatant.

Cyclodextrin inclusion can be carried out by adding a solution prepared by heat-dissolving cyclodextrin in water or the like to a solution prepared by dissolving the substance of interest in a solvent, and then filtering the precipitate precipitated by cooling and sterilizing and drying the same. Regarding the cyclodextrin to be used in this case, cyclodextrins having different void diameter ($\alpha$, $\beta$, and $\gamma$ types) may be optionally selected according to said substance.

The solutions for injection can be prepared using a carrier consisting of a salt solution, a glucose solution or a mixture of a salt solution and a glucose solution.

The suspensions can be produced using water, sucrose, sorbitol, fructose and the like saccharides, polyethylene glycol and the like glycols and oils.

Preparation of Fat Emulsions can be Carried Out, for example, by mixing the substance of interest, an oil component (soybean oil, sesame oil, olive oil or the like plant oil, MCT or the like), an emulsifying agent (phospholipid or the like) and the like, making them into a solution with heating, and then adding a necessary amount of water thereto and emulsifying and homogenizing the solution using an emulsifier (a homogenizer such as a high pressure jet type, an ultrasonic type or the like). In addition, it is possible to freeze-dry them. In this connection, an emulsification assisting agent may be added when fat emulsions are prepared, and for example, glycerol and saccharides (e.g., glucose, sorbitol, fructose and the like) can be exemplified as the emulsification assisting agent.

Powders, pills, capsules, tablets, granules, fine subtilaes, drip infusions, suppositories, inhalations, eye lotions, ear lotions, ointments, creams, percutaneous absorption preparations, transmucosal absorption preparations and the like can also be prepared by generally used methods.

EXAMPLES

The following describes the invention further illustratively based on examples, though the invention is not limited to the following examples.
(Identification of Gene Whose Expression is Elevated in Colon Cancer Cell in Comparison with Normal Colon Cell)

The gene whose expression is elevated in the cancer cell in comparison with the normal cell was identified making use of the microarray data base of Bioexpress (Genelogic). Expression profile data in respective cells of 117 normal colon tissue cell samples and 77 colon cancer cell samples are contained in the microarray data base. The expression profile data are housed as expression data base of respective cells using Affimetrix human gene oligonucleotide chip HG-U133. Among the genes whose expressed amounts are larger in colon cancer cells than in normal colon cells, a gene concerned in the DNA to be provided by the invention, in which full-length nucleotide sequence of the gene is not registered in the nucleotide data base (DDBJ/EMBL/GenBank), was identified. Ratio of the average expression of the gene concerned in the DNA to be provided by the invention in the 77 colon cancer cell samples to the average expression of the gene concerned in the DNA to be provided by the invention in the 117 normal colon tissue cell samples was about 2.38. The significance level was less than 0.0000001. When the ratio of expression of the gene concerned in the DNA to be provided by the invention was examined in the same manner for other cancer cells, the result showed an expression ratio of about 1.22 (significance level 0.00243) in the case of breast cancer, about 1.52 (significance level less than 0.0000001) in the case of lung cancer, about 1.98 (significance level 0.00003) in the case of gastric cancer, and about 1.37 (significance level 0.0019) in the case of cancer of the pancreas.

(Preparation of Gene)

As a gene corresponding to the probe sequence information of the microarray data base, nucleotide sequence of N-terminal deficient DNA of the gene concerned in the DNA to be provided by the invention was registered in the public nucleotide data base (DDBJ/EMBL/GenBank). Thus, the nucleotide sequence of N-terminal DNA of the gene concerned in the DNA to be provided by the invention was not clear.

Accordingly, complete sequence of the DNA to be provided by the invention was determined in the following manner. To begin with, complete sequence of the DNA to be provided by the invention was estimated. Firstly, homology retrieval was carried out on the nucleotide data base (DDBJ/EMBL/GenBank) using a nucleotide sequence concerned in the 5'-end 30 polynucleotide of the N-terminal deficient DNA as the query. As a result of the retrieval, it showed a high homology with a human genomic DNA fragment (accession No. AL035086). Among the nucleotide sequence of human genomic DNA fragment, a nucleotide sequence obtained by removing partial sequences having homology with the nucleotide sequence of N-terminal deficient DNA (to be referred to as nucleotide sequence A hereinafter) was used as the object to identify the initiation codon existing in the most 5'-end side among initiation codons contained in the nucleotide sequence A, and to identify the partial sequence in and after said initiation codon of the nucleotide sequence A (to be referred to as estimated N-terminus nucleotide sequence hereinafter). It was estimated that sequence length of the estimated N-terminus nucleotide sequence was 183, and this is a partial sequence coding for 61 amino acid. In addition, a homology retrieval was carried out on the nucleotide data base (DDBJ/EMBL/GenBank) using a sequence prepared by converting the nucleotide sequence of N-terminal deficient DNA into amino acid sequence as the query. As a result, it showed high homology with a DNA concerned in a gene estimated to be a mouse ortholog of the gene concerned in the DNA to be provided by the invention. When homology retrieval was carried out between a sequence prepared by converting a 5'-end partial sequence (sequence length 183) of said DNA into amino acid sequence and a sequence prepared by converting the estimated N-terminal nucleotide sequence into amino acid sequence, they showed a good homology (56.1%). Accordingly, it was estimated that the estimated N-terminal nucleotide sequence is the nucleotide sequence of N-terminal moiety DNA.

In addition, cDNA cloning of the gene concerned in the DNA to be provided by the invention was carried out. The DNA consisting of the nucleotide sequence described in SEQ ID NO:3 of the SEQUENCE LISTING was used as the sense primer, and the DNA consisting of the nucleotide sequence described in SEQ ID NO:4 of the SEQUENCE LISTING as the antisense primer. QUICK-Clone cDNA (Clontech) was used as the template, and KOD-Plus-DNA polymerase (TOYOBO) was used as the DNA polymerase. In the PCR amplification reaction, a step consisting of 94° C. for 2 minutes, 94° C. for 30 seconds and 68° C. for 4 minutes was carried out 40 cycles, subsequently carrying out a treatment at 68° C. for 3 minutes. The thus obtained amplification product was ligated to pCR4Blunt-TOPO Vector (TOYOBO). Determination of the DNA concerned in the instant gene contained in the thus obtained recombinant vector (to be referred to as recombinant pCR4Blunt-TOPO Vector concerned in the DNA to be provided by the invention hereinafter) was carried out using Long-Read Tower (Amersham Biosciences). As a result, it was revealed that the nucleotide sequence of DNA concerned in the instant gene is the nucleotide sequence described in SEQ ID NO:1 of the SEQUENCE LISTING.

(Comparison of Expressed Amounts in Normal Colon Cell and Colon Cancer Cell)

A finding that the amount of transcription product of the gene concerned in the DNA to be provided by the invention in normal colon cell is smaller than the amount of transcription product of the gene concerned in the DNA to be provided by the invention in colon cancer cell was confirmed by the following procedure. Firstly, colon cancer cells HCT 116 and SW 620 were purchased from Dainippon Pharmaceutical, and both cells were cultured using DMEM (Invitrogen) containing 10% fetal calf serum (FCS, Iwaki Glass). On the other hand, a normal colon epithelial cell CCD841CoN was purchased from American Tissue Culture Collection, and said cell was cultured using ACL-4 serum-free medium. Total RNA was extracted from these cells using Isogen (Nippon Gene). Using RNA PCR Kit (AMV) Ver.2.1 (TAKARA), reverse transcription reaction from 1 μg of the total RNA was carried out under a condition of 30° C. for 10 minutes, 42° C. for 30 minutes, 99° C. for 5 minutes and 5° C. for 5 minutes. Next, PCR amplification reaction of the cDNA obtained by the reverse transcription reaction was carried out. The reaction was carried out by adding a primer consisting of the nucleotide sequence described in SEQ ID NO:5 of the SEQUENCE LISTING and a primer consisting of the nucleotide sequence described in SEQ ID NO:6 of the SEQUENCE LISTING to a solution in which ¹/₁₀ of the obtained cDNA was dissolved, and using Advantage polymerase mix (Clontech). The reaction condition was 94° C. for 1.5 minutes, followed by 30 cycles of 94° C. for 30 seconds, 60° C. for 30 seconds and 72° C. for 1 minute, and final treatment at 72° C. for 3 minutes. The reaction solution was applied to 1% agarose gel to carry out electrophoresis. After the electrophoresis, the PCR amplification product was detected by ethidium bromide staining.

As a control, expression of glyceraldehyde 3-phosphate dehydrogenase was detected by the same method. As a result, a significant difference was not found between the normal colon cell and colon cancer cell regarding the expressed amount of the control glyceraldehyde 3-phosphate dehydrogenase. However, regarding the expressed amount of the gene concerned in the DNA to be provided by the invention, it was revealed that the expressed amount in the colon cancer cell is larger than the expressed amount in the normal colon cell (FIG. 4).

(Preparation of Protein)

The protein encoded by the instant gene was expressed by culturing an animal cell into which an expression vector integrated with the DNA concerned in the instant gene had been introduced, and its molecular weight was measured using western blotting. A pCMV-Tag4 Vector (Stratagene) was used as the expression vector. The recombinant pCR4Blunt-TOPO Vector concerned in the DNA to be provided by the invention was digested with BamHI and XhoI, and the thus obtained DNA fragment was mixed with the pCMV-Tag4 Vector which had been digested with BamHI and XhoI, thereby obtaining an expression vector into which the DNA concerned in the instant gene (to be referred to as hC1S hereinafter) was integrated (to be referred to as recombinant pCMV-Tag4 Vector concerned in the DNA to be provided by the invention hereinafter). The 293 cell was used as the animal cell. Firstly, the 293 cell was cultured using DMEM medium (Invitrogen) containing 10% FCS, until reaching a sub-confluent state. After the culturing, the medium was changed to Opti MEMI (Invitrogen). After the exchange, 4 μg of the recombinant pCMV-Tag4 Vector concerned in the DNA to be provided by the invention was transferred into the 293 cell by the lipofection method using Lipofect Amine Plus (Invitrogen). As a control, pCMV-Tag4 Vector into which the instant gene was not integrated was transferred into the 293 cell by the lipofection method using Lipofect Amine Plus (Invitrogen).

After a lapse of 5 hours from the transfer, Opti MEMI medium containing 20% FCS was added to the culture medium of gene-transferred cell, in such an amount that the final serum concentration of the culture medium became 10%. Further on the next day, the medium of the gene-transferred cell was changed to the DMEM medium containing 10% FCS. After a lapse of 48 hours from the gene transfer, the gene-transferred cells were lysed by adding a solution for cell lysis (1% Triton X, 50 mM Tris-HCl pH 7.4, 300 mM NaCl, 5 mM EDTA and complete protease inhibitor cocktail EDTA-free, Roche). After allowing to stand for 30 minutes on ice, the solution (to be referred to as post-lysis solution hereinafter) was recovered and centrifuged (15,000 rpm, 15 minutes). After the centrifugation treatment, BSA-treated IgG agarose gel (Sigma) was added to the supernatant and allowed to stand overnight at 4° C. On the next day, anti-FLAG M2 agarose gel (Sigma) was added to the supernatant to carry out the antigen-antibody reaction at 4° C. for 3.5 hours, and then washed 3 times with a washing liquid (0.1% Triton X, 50 mM Tris-HCl pH 7.4, 300 mM NaCl and 5 mM EDTA) and then once with a phosphate buffer. The protein linked to the anti-FLAG M2 agarose gel was recovered using a sample buffer liquid containing 10% 2-mercaptoethanol. The recovered solution and the post-lysis solution were applied to a 4-20% SDS gel to carry out electrophoresis. After the electrophoresis, the electrophoresis products were transferred onto a nitrocellulose filter (Scleicher and Shcuell). After the transfer, BSA blocking was carried out, and the electrophoresis products were allowed to react with an anti-FLAG M2 antibody (Sigma) and an anti-mouse Ig antibody (Amersham) labeled with hydrogen peroxide dehydrogenase and then to develop color with 4-chloro-1-naphthol. When the post-lysis solution was directly used without immunoprecipitation, it was not able to detect the protein to be provided by the invention. However, in the case of effecting immunoprecipitation with the anti-FLAG M2 agarose gel, it was able to detect the protein to be provided by the invention. As a result of the detection, it was revealed that molecular weight of the protein to be provided by the invention is about 110 kDa (FIG. 5).

(Cell Growth Enhancing Activity of Protein Encoded by the Gene Concerned in the DNA to be Provided by the Invention)

Using DMEM medium containing 10% FCS, the 293 cell was inoculated into 24 and 12 well plates and cultured until a sub-confluent state. After the culturing, 0.4 μg (24 well) or 0.7 μg (12 well) of the recombinant pCMV-Tag4 Vector concerned in the DNA to be provided by the invention was transferred into the 293 cell using Lipofect Amine Plus (Invitrogen). As a control, pCMV-Tag4 Vector into which the gene concerned in the DNA to be provided by the invention was not integrated was transferred into the 293 cell using Lipofect Amine Plus (Invitrogen). On the next day, the cells were spread on a 10 cm plate of DMEM containing 10% FCS, and G418 (Promega) was added to a final concentration of 1 mg/ml. Formation of colonies was effected by carrying out the culturing for 10 to 14 days while exchanging the medium containing 1 mg/ml in concentration of G418 (Promega) every 3 or 4 days. The formed colonies were stained with 0.2% Crystal Violet. As a result, it was found that the cell growth is accelerated when the gene concerned in the DNA to be provided by the invention is forcedly expressed by transferring it into the cell. This result shows that the protein encoded by the gene concerned in the DNA to be provided by the invention has the cell growth accelerating activity (FIG. 6).

(Intracellular Localization of the Protein Encoded by the Gene Concerned in the DNA to be Provided by the Invention)

Intracellular localization of the protein encoded by the gene concerned in the DNA to be provided by the invention was determined by the following procedure. The recombinant vector, pCMV-Tag4, concerned in the DNA to be provided by the invention was transferred by the aforementioned method into the 293 cell of a sub-confluent state in a 10 cm plate. After 48 hours, resulting cells were recovered into 0.5 ml of a mitochondria isolation buffer (MIB; 200 mM mannitol, 70 mM sucrose, 35 mM 2-mercaptoethanol, 5 mM EDTA, 50 mM potassium phosphate, complete protease inhibitor cocktail EDTA-free, pH 7.3). The cells were disrupted and suspended using a homogenizer, and then centrifugation precipitation was carried out twice at 600 g at 4° C. The supernatant was further centrifuged at 15000 rpm at 4° C. for 20 minutes. Each of the supernatant (cytoplasm fraction) and precipitate (mitochondria fraction), in an amount corresponding to ⅕ of the first suspension, was subjected to the aforementioned western blotting using an anti-FLAG antibody or to a western blotting using an anti-mitochondria HSP 70 antibody (1/500 dilution, Affinity Bioreagent). A band considered to be the protein encoded by the gene concerned in the DNA to be provided by the invention was detected only in the mitochondria fraction, showing the mitochondria localization predicted from the sequence analysis of the instant gene (FIG. 7, upper row). In addition, the anti-mitochondria HSP 70 was also detected only in the mitochondria fraction, thus proving validity of the fractionation procedure (FIG. 7, lower row).

(Signal Peptide Cutting Site of the Protein Encoded by the Gene Concerned in the DNA to be Provided by the Invention)

By the aforementioned method, the protein encoded by the gene concerned in the DNA to be provided by the invention was expressed in the 293 cell, purified by anti-FLAG M2 agarose gel and separated by 4-20% SDS gel electrophoresis. Thereafter, proteins in the gel were transferred onto a PVDF membrane (Pharmacia) and stained with Coomassie R 250 Solution. The N-terminus of a protein which is shown by a band of around 110 kDa and is also considered to be the protein encoded by the gene concerned in the DNA to be provided by the invention was determined at Toray Research Center. The result was SSGGG, and as expected, this was cut off at the position considered to be the mitochondria target sequence (between 31st Ala and 32nd Ser of SEQ ID NO:2).

(Superiority as the Target of the Gene Concerned in the DNA to be Provided by the Invention to DHFR, TS and the Like Existing Antitumor Agent Targets, Based on the Expression Patterns)

Expression patterns of existing antitumor agent targets dihydrofolate reductase (DHFR: target of methotrexate) and thymidylate synthase (TS: target of 5-fluorouridine) and the gene concerned in the DNA to be provided by the invention in human organs were compared using the microarray data base of Bioexpress (FIG. 8). In comparison with the normal colon tissue, expression strength in the colon cancer was 1.1 times increase by the DHFR gene, and 1.5 times by the TS gene. On the other hand, expression of the gene concerned in the DNA to be provided by the invention was elevated 2.38 times as described in the foregoing. In addition, in taking note of the thymus which is a normal tissue holding a large number of proliferating cells, expression of the DHFR gene therein showed a value of 2.5 times of that in the normal colon tissue. In the same manner, expression of the TS gene in the thymus showed a value of 5.5 times. Since expression of these genes is high in the thymus, it is considered that side effects of antitumor agents, methotrexate and 5-fluorouridine, which target these genes are apt to be expressed. However, expression of the gene concerned in the DNA to be provided by the invention in the thymus showed a value of 1.4 times of that in the normal colon tissue. Thus, in the case of the gene concerned in the DNA to be provided by the invention, its expression is elevated in the cancer tissue, and what is more, its significantly high expression is not found in the thymus or the like tissue where expression of genes generally concerned in its growth (e.g., DHFR and TS genes) increases. Accordingly, the gene concerned in the DNA to be provided by the invention can be regarded as a more advantageous antitumor agent target than the other 2 antitumor agent targets compared herein, in terms of the provision of an antitumor agent having less side effects and the like.

(Activation of C1 Metabolism Through Wnt Pathway in Mitochondria and usefulness of the gene of the invention, in the Carcinogenic Process of Colon Cancer)

In the case of colon cancer, it is considered that the cancer is developed through the shifting from a polyp-like precancerous state to cancerous state due to a gene expression disturbance caused by β catenin (Non-patent Reference 11). A mutation which induces activation of the Wnt gene signal pathway, in other words, a mutation that inactivates the APC gene or activates β catenin, results in the nuclear accumulation of β catenin and further causes formation of a complex of β catenin and a transcription factor Tcf/LEF. It is known that the mutation which induces activation of the Wnt gene signal pathway is found in about 90% of colon cancer cases (Non-patent Reference 12). A c-myc oncogene is present as one of the target genes of this β catenin pathway (Non-patent Reference 13). The myc is an important transcription factor which is concerned in cell growth, differentiation and apoptosis (Non-patent Reference 14), but its detailed mechanism is not clear yet. Recently, it has been revealed that mitochondrial serine hydroxymethyltransferase (mt SHMT) gene is a target gene of myc (Non-patent References 15 and 16), and this gene product is concerned in the one carbon unit metabolism together with C1-THFS, by catalyzing the reaction to synthesize glycine and 5,10-methylene-tetrahydrofolic acid from serine and tetrahydrofolic acid or its reverse reaction. In addition, a clone called U06665 has been identified in another study as a gene in which c-myc induces transcription in mouse (Non-patent Reference 17), and it has been revealed by the analysis of the inventor that this gene is a part of a mouse ortholog of the gene concerned in the DNA to be provided by the invention. When these facts are synthetically considered, it is very reasonable to think that a group of genes cooperating with one another in the same intracellular region, namely mitochondria, and in one metabolic pathway are under control of a cooperative gene. Accordingly, the inventor thinks that the phenomenon in which the carbon unit metabolism of mitochondria is activated by the activation of Wnt signal pathway is playing an important role in the developing process of colon cancer (FIG. 9). The gene concerned in the DNA to be provided by the invention can be regarded as a gene which forms the basis of this process, so that it can become an antitumor agent target (Non-patent Reference 20).

While the invention has been described in detail and with reference to specific embodiments thereof, it will be apparent to one skilled in the art that various changes and modifications can be made therein without departing from the spirit and scope of the invention.

This application is based on a Japanese patent application filed on Sep. 30, 2003 (Japanese Patent Application No. 2003-341245), the entire contents thereof being thereby incorporated by reference.

<Industrial Applicability>

The invention provides a novel C1-THFS gene whose expression is elevated in cancer cells in comparison with normal cells. The DNA concerned in the instant gene encodes a protein having cell growth accelerating activity. Provision of a novel pharmaceutical composition and a diagnosis means making use of this characteristic property provides a great usefulness in the clinical and fundamental medical field of colon cancer.

<Sequence Listing Free Text>

SEQ ID NO:1: (1): (2934) a region coding for the complete length of the instant protein SEQ ID NO:1: (1): (183) N-terminal moiety DNA SEQ ID NO:1: (184): (2934) N-terminal deficient DNA

The invention claimed is:

1. A method for identifying a compound that inhibits the cell growth accelerating activity of a tetrahydrofolate synthetase protein, wherein said protein comprises residues 1-978 of SEQ ID NO: 2, or comprises residues 32-978 of SEQ ID NO: 2, wherein said method comprises the steps of comprising:
   (i) contacting a cell expressing said protein with a test compound under conditions which permit interaction between said protein and said test compound;
   (ii) culturing said cell and determining the growth rate of said cell during said culturing; and
   (iii) determining that the test compound inhibits the cell growth accelerating activity of said protein when the growth rate of said cell in the presence of said test compound is reduced in comparison to the growth rate of the cell in the absence of said test compound.

2. The method according to claim 1, wherein the growth rate of said cell is determined by counting the number of grown cells after the culturing.

* * * * *